United States Patent
Tamper et al.

(10) Patent No.: US 11,046,983 B2
(45) Date of Patent: *Jun. 29, 2021

(54) METHOD AND AN APPARATUS FOR AN ENZYMATIC HYDROLYSIS, A LIQUID FRACTION AND A SOLID FRACTION

(71) Applicant: UPM-KYMMENE CORPORATION, Helsinki (FI)

(72) Inventors: Juha Tamper, Levänen (FI); Sami Turunen, Lappeenranta (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/305,924

(22) PCT Filed: Jun. 1, 2017

(86) PCT No.: PCT/FI2017/050411
§ 371 (c)(1),
(2) Date: Nov. 30, 2018

(87) PCT Pub. No.: WO2017/207877
PCT Pub. Date: Dec. 7, 2017

(65) Prior Publication Data
US 2019/0127771 A1    May 2, 2019

(30) Foreign Application Priority Data

Jun. 3, 2016  (FI) ..................... 20165466

(51) Int. Cl.
*C12P 19/14* (2006.01)
*C12P 19/02* (2006.01)
*C12M 1/40* (2006.01)
*C12P 19/00* (2006.01)
*C13K 1/02* (2006.01)

(52) U.S. Cl.
CPC ............ *C12P 19/14* (2013.01); *C12M 21/18* (2013.01); *C12P 19/00* (2013.01); *C12P 19/02* (2013.01); *C13K 1/02* (2013.01); *Y02E 50/10* (2013.01); *Y02P 20/582* (2015.11)

(58) Field of Classification Search
CPC .................................................... C12M 21/18
See application file for complete search history.

(56) References Cited

U.S. PATENT DOCUMENTS

| | | |
|---|---|---|
| 2010/0136634 A1 | 6/2010 | Kratochvil |
| 2012/0107920 A1 | 5/2012 | Taneda |
| 2015/0136120 A1 | 5/2015 | Torre |

FOREIGN PATENT DOCUMENTS

| | | | |
|---|---|---|---|
| EA | 201000275 A1 | 8/2010 | |
| EP | 2548965 A1 | 1/2013 | |
| RU | 2432368 C2 | 8/2009 | |
| WO | 2007009463 A2 | 1/2007 | |
| WO | 2007147263 A1 | 12/2007 | |
| WO | WO2012155238 | * 11/2012 | ............... C12P 7/02 |
| WO | 2013103138 A1 | 7/2013 | |
| WO | 2014144565 A1 | 9/2014 | |
| WO | 2016124822 A1 | 8/2016 | |

OTHER PUBLICATIONS

Visser et al: "Increased enzymatic hydrolysis of sugarcane bagasse from enzyme recycling", Biotechnology for Biofuels, vol. 8, 2015,pp. 1-9.
Weiss et al: "Enzymatic lignocellulose hydrolysis: Improved cellulase productivity by insoluble solids recycling",Biotechnology for Biofuels,vol. 6, 2013,pp. 1-14.
Kinnarinen et al: "Solid-liquid separation of hydrolysates obtained from enzymatic hydrolysis of cardboard waste", Industrial Crops and Products,vol. 38, 2012, pp. 72-80.
Kinnarinen et al: "Use of filter aids to improve the filterability of enzymatically hydrolyzed biomass suspensions", Industrial & Engineering Chemistry Research, vol. 52, 2013, pp. 14955-14964.
Jorgensen et al: "Enzyme recycling in lignocellulosic biorefineries", Biofuel,Bioproducts & Biorefining, vol. 11, Oct. 18, 2016 (Oct. 18, 2016), pp. 150-167.
Pihlajaniemi V. et al. Enzymatic saccharification of pretreated wheat straw: Comparison of solids-recycling, sequential hydrolysis and batch hydrolysis. Bioresource technology, 2014. vol. 153, p. 15-22.
International Search Report from International Application No. PCT/FI2017/050411 dated Sep. 19, 2017.
Search Report from Patent Application No. 20165466 dated Dec. 22, 2016.
Russian Office Action in Russian Patent Application No. RU2018145211/10, dated Dec. 24, 2020 (6 pages).

* cited by examiner

*Primary Examiner* — Bin Shen
(74) *Attorney, Agent, or Firm* — Nixon Peabody LLP

(57) ABSTRACT

In a method and an apparatus for an enzymatic hydrolysis in which plant based raw material is hydrolysed by means of enzymes in at least one enzymatic hydrolysis stage. A plant based feed (1) is fed to the enzymatic hydrolysis stage (2) in which the plant based feed is hydrolysed. A liquid fraction (3) comprising carbohydrates is separated from a solid fraction (4) in a solid-liquid separation stage (11). At least a part (5) of the solid fraction (4) comprising enzymes is recirculated to the plant based feed (1) of the enzymatic hydrolysis stage (2) or to the enzymatic hydrolysis stage (2), and a rest part (6) of the solid fraction (4) is recovered. Further, the invention relates to the liquid fraction and the solid fraction and their use.

15 Claims, 8 Drawing Sheets

METHOD AND AN APPARATUS FOR AN ENZYMATIC HYDROLYSIS, A LIQUID FRACTION AND A SOLID FRACTION

CROSS-REFERENCE TO RELATED APPLICATIONS

This application is a U.S. National Stage of International Patent Application No. PCT/FI2017/050411, filed Jun. 1, 2017, which claims priority to Finnish Patent No. 20165466, filed Jun. 3, 2016, both of which are hereby incorporated by reference in their entireties.

FIELD

The invention relates to a method and an apparatus for an enzymatic hydrolysis. Further, the invention relates to a liquid fraction and a solid fraction and their use.

BACKGROUND

It is known different methods for forming carbohydrates and lignin from different raw materials, such as biomass. Many bio-refinery processes, e.g. hydrolysis, generate lignin and sugars after the treatment of the biomass. It is known to use an enzymatic hydrolysis in the bio-refinery processes.

OBJECTIVE

The objective of the invention is to improve an enzymatic hydrolysis. Another objective is to provide a new method for carrying out the enzymatic hydrolysis. Another objective is to produce a liquid fraction and a solid fraction in connection with the enzymatic hydrolysis. Another objective is to decrease an enzyme dosage.

SUMMARY

A method for an enzymatic hydrolysis in which wood based material is hydrolysed using enzymes in at least one enzymatic hydrolysis stage, is disclosed. The method includes pretreating the wood based material using a combination of hydrolysis and steam explosion to form a wood based feed wherein the wood based feed comprises cellulose based material. The method further includes feeding the wood based feed to the enzymatic hydrolysis stage in which the wood based feed is hydrolysed. The method further includes separating a liquid fraction comprising carbohydrates from a solid fraction in a solid-liquid separation stage wherein most of the enzymes are attached to the solid fraction. The method further includes recirculating at least a part of the solid fraction comprising the enzymes to the wood based feed of the same or previous enzymatic hydrolysis stage. The method further includes recovering a rest part of the solid fraction.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION

Figure 1:
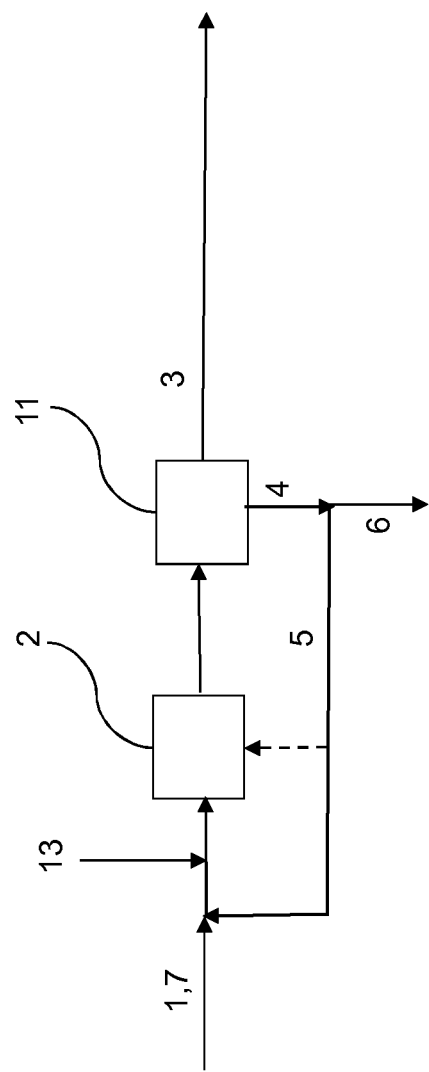
FIG. 1 is a flow chart illustration of a method according to one embodiment.

In a method for an enzymatic hydrolysis plant based material, preferably cellulose based material, is hydrolysed by means of enzymes in at least one enzymatic hydrolysis stage. In the method a plant based feed (1), which may be plant based raw material (7) or a solid fraction (4) from any enzymatic hydrolysis stage or a previous enzymatic hydrolysis stage, is fed to the enzymatic hydrolysis stage (2) in which the plant based feed is hydrolysed. A liquid fraction (3) comprising carbohydrates is separated from a solid fraction (4) in a solid-liquid separation stage (11). At least a part (5) of the solid fraction (4) comprising enzymes, e.g. at least a part of at least one solid fraction comprising enzymes, is recirculated to the plant based feed (1) of the enzymatic hydrolysis stage (2) or to the enzymatic hydrolysis stage (2), in one embodiment to the plant based feed (1) of any enzymatic hydrolysis stage (2,8,17), such as the same or previous enzymatic hydrolysis stage or a next enzymatic hydrolysis stage, or to any enzymatic hydrolysis stage (2,8,17), such as back to the same or previous enzymatic hydrolysis stage or to a next enzymatic hydrolysis stage. A rest part (6) of the solid fraction (4), e.g. at least a part of at least one solid fraction, is recovered. The rest part of solid fraction may be utilized as a component in a product or in an intermediate product, or it may be supplied to the next enzymatic hydrolysis stage or further processing stage, or it may be supplied to a storage, or it may be processed by means of other treatment. In one embodiment, the liquid fraction is supplied out from the solid-liquid separation stage.

Figure 2:
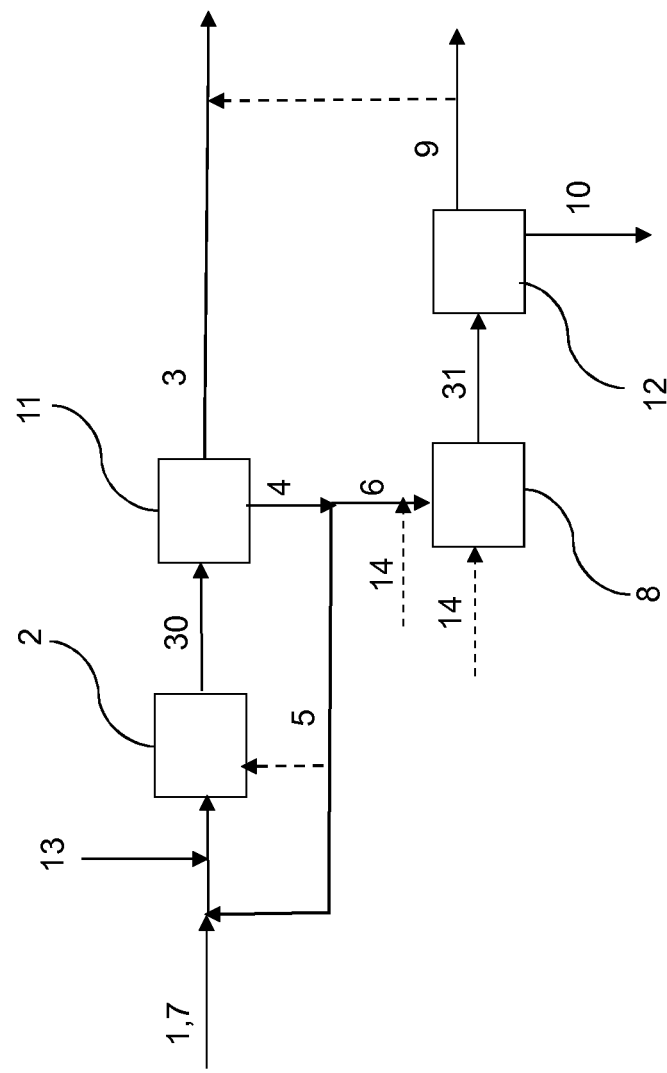
FIG. 2 is a flow chart illustration of a method according to another embodiment.
Figure 3:
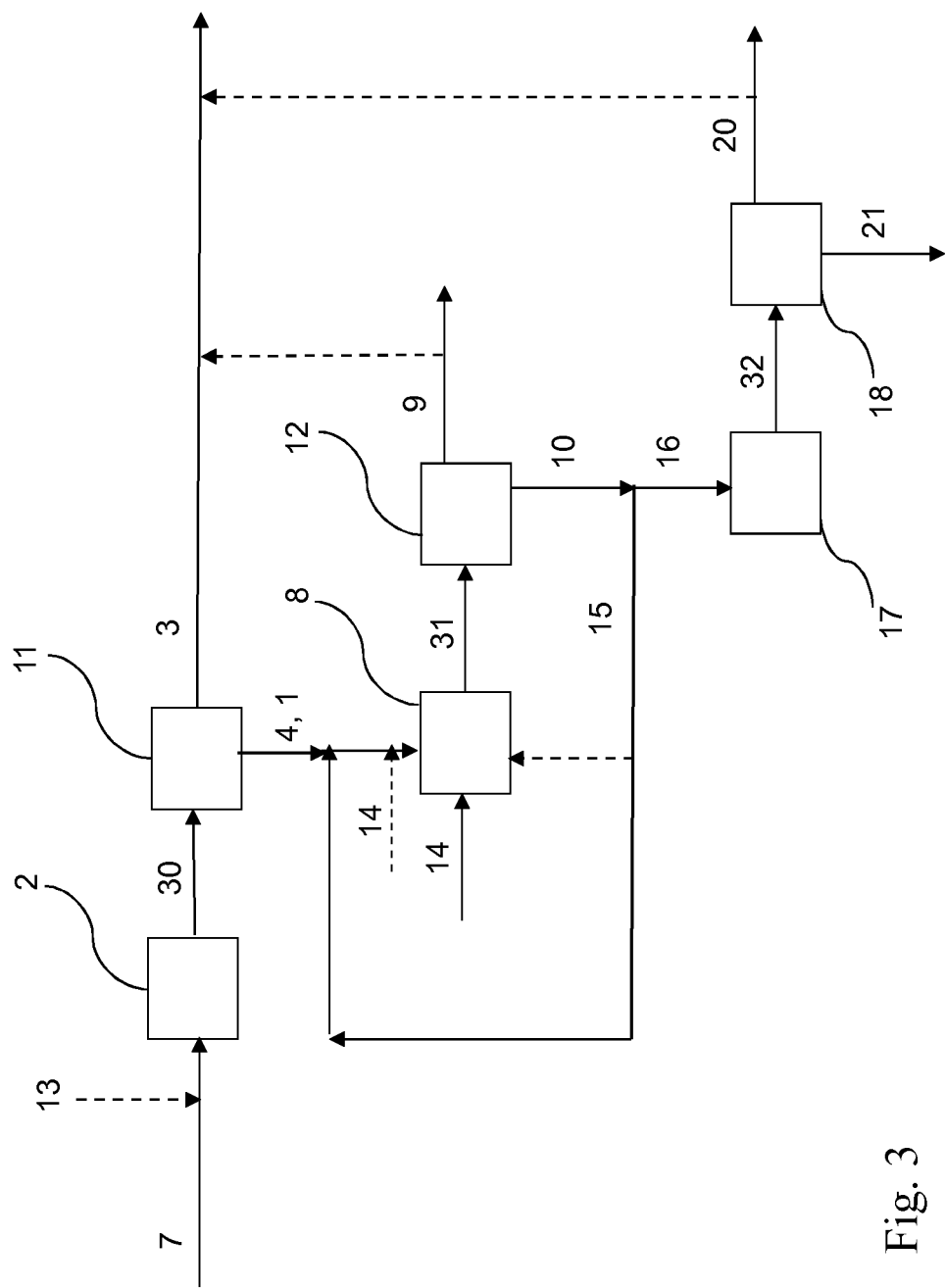
FIG. 3 is a flow chart illustration of a method according to another embodiment.
Figure 4:
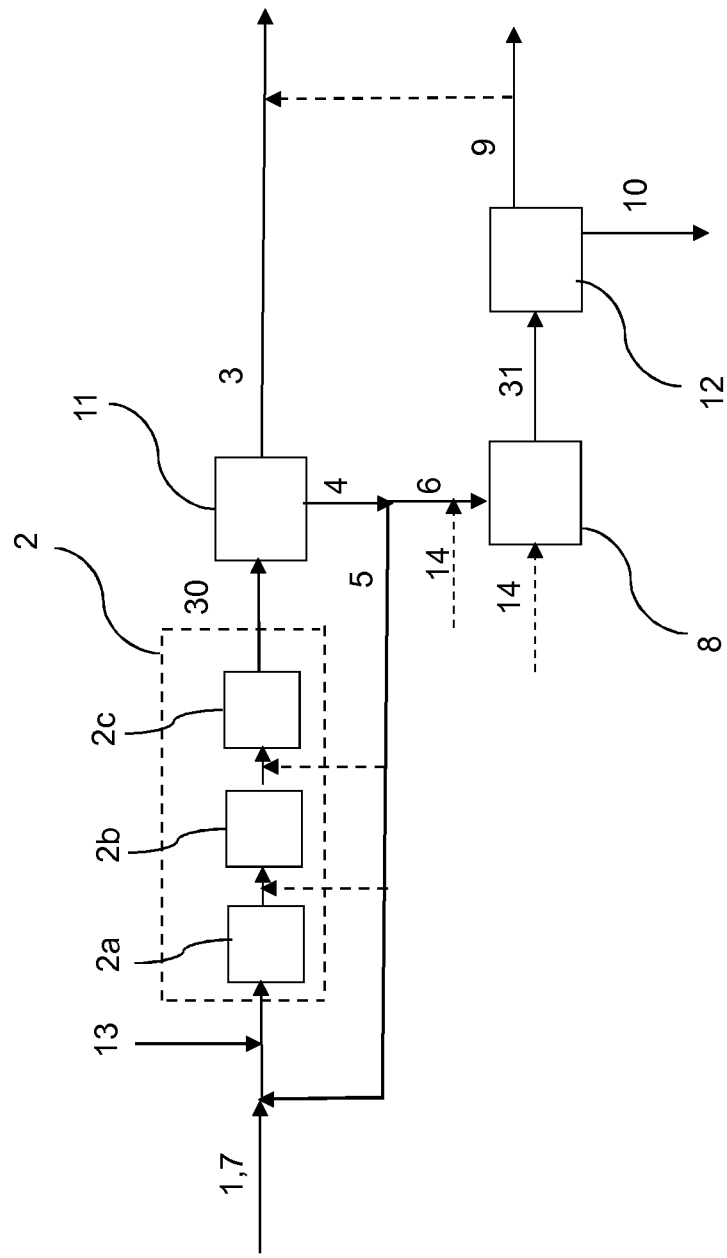
FIG. 4 is a flow chart illustration of a method according to another embodiment.
Figure 5:
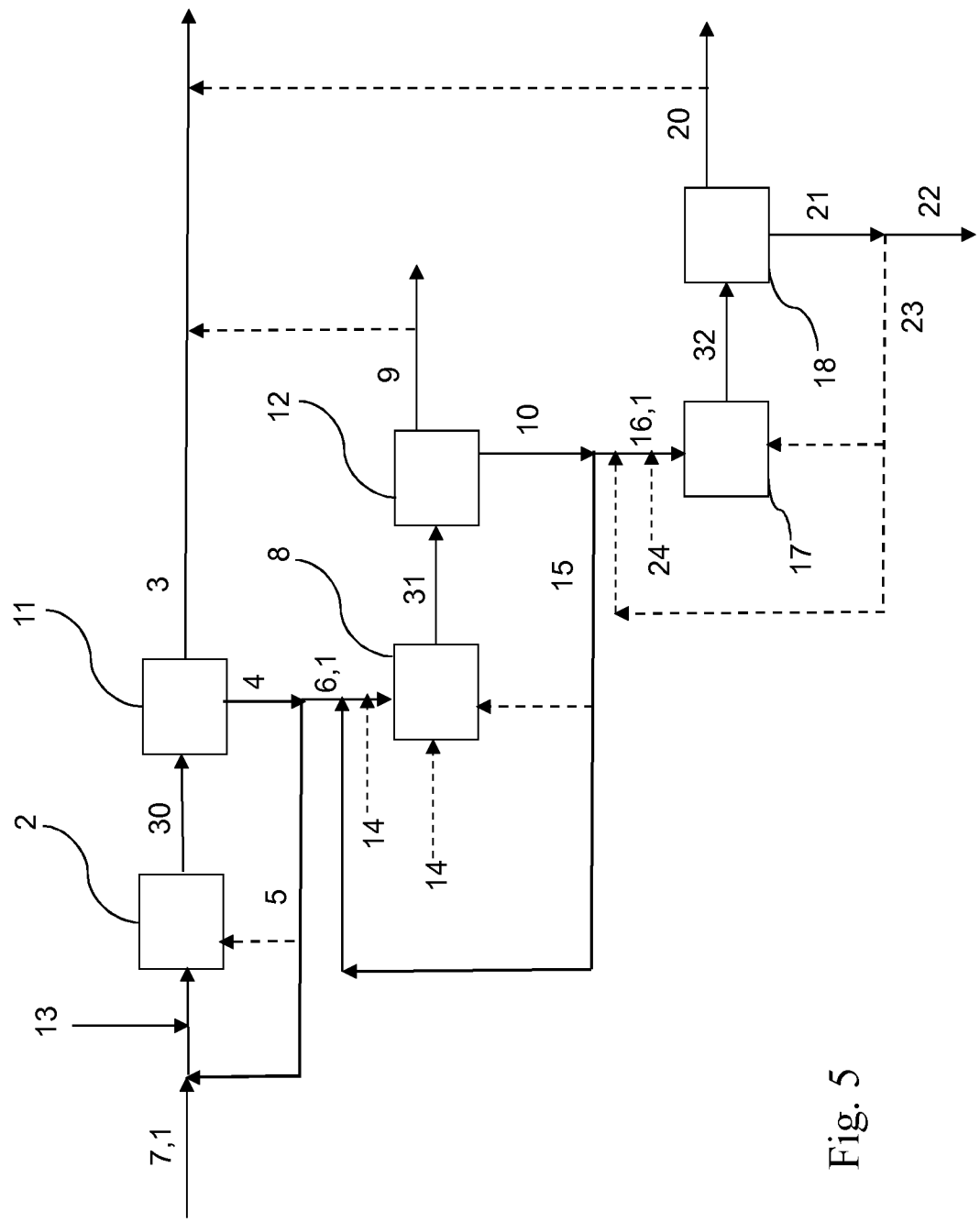
FIG. 5 is a flow chart illustration of a method according to another embodiment.

One embodiment of the method is shown in FIG. 1. Another embodiment of the method is shown in FIG. 2. Another embodiment of the method is shown in FIG. 3. Another embodiment of the method is shown in FIG. 4. Another embodiment of the method is shown in FIG. 5.

The apparatus comprises at least one enzymatic hydrolysis stage (2), at least one feeding device for feeding a plant based feed (1), which may be plant based raw material (7) or a solid fraction (4) from any enzymatic hydrolysis stage or a previous enzymatic hydrolysis stage, to the enzymatic hydrolysis stage (2) in which the plant based feed is hydrolysed, at least one solid-liquid separation stage (11) in which a liquid fraction (3) comprising carbohydrates is separated from a solid fraction (4), and at least one recirculation device for recirculating at least a part (5) of the solid fraction (4) comprising enzymes to the plant based feed (1) of the enzymatic hydrolysis stage (2) or to the enzymatic hydrolysis stage (2), in one embodiment to the plant based feed (1) of any enzymatic hydrolysis stage (2,8,17), such as the same or previous enzymatic hydrolysis stage or a next enzymatic hydrolysis stage, or to any enzymatic hydrolysis stage (2,8,17), such as back to the same or previous enzymatic hydrolysis stage or to a next enzymatic hydrolysis stage.

Further, the apparatus may comprise at least one means for recovering a rest part (6) of the solid fraction (4), e.g. means for supplying the rest part of the solid fraction out from the apparatus or means for supplying the rest part of the solid fraction to the next enzymatic hydrolysis stage or other treatment stage.

In this context, an enzymatic hydrolysis means any enzymatic hydrolysis. In one embodiment, the enzymatic hydrolysis is an enzymatic hydrolysis of carbohydrates, e.g. cellulose.

In this context, a liquid fraction (3,9,20) means a liquid or a liquid composition, which comprises mainly soluble carbohydrates and which is separated from the solid fraction. In a preferred embodiment, the liquid fraction includes carbohydrates, preferably C6 carbohydrates ($C_6H_{12}O_6$ or $C_6(H_2O)_n$). Further, the liquid fraction may include C5 carbohydrates ($C_5H_{10}O_5$ or $C_5(H_2O)_n$). The liquid fraction may comprise carbohydrates, such as monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or ($C_5H_8O_4)_n$). In one embodiment, the liquid fraction comprises soluble C5 and C6 carbohydrates and other carbohydrates. In one embodiment, the liquid fraction comprises soluble C5 carbohydrates and other carbohydrates. In one embodiment, the liquid fraction comprises soluble C6 carbohydrates and other carbohydrates. The liquid fraction may comprise also other components.

In this context, a solid fraction (4,10,21) or its part means any solid fraction comprising solids, such as solid material, e.g. solid cake, high consistency slurry, agglomerates or the like, when a liquid fraction has been separated from the solid fraction. However, some liquid or moisture is remaining in the solid fraction. In a preferred embodiment, the solid fraction comprises lignin. Further, the solid fraction comprises carbohydrates, e.g. solid C6 carbohydrates ($C_6H_{12}O_6$ or $C_6(H_2O)_n$). The solid fraction may comprise also other carbohydrates and other components.

In this context, plant based feed (1) means any plant based feed. In one embodiment, the plant based feed is plant based raw material (7). In one embodiment, the plant based feed is a solid fraction (4,6,10,16,21,22) from a previous treatment stage, e.g. from a previous enzymatic hydrolysis stage, or from any enzymatic hydrolysis stage (2,8,17).

In this context, plant based raw material (7) means any plant based raw material, e.g. wood based raw material and/or other plant based material. Preferably, the plant based raw material is cellulose based material. The plant based raw material includes lignin, cellulose and hemicellulose. In one embodiment, the plant based raw material is formed from material selected from the group consisting of wood based material, wood, lignocellulosic biomass, agricultural residues, bagasse based material, sugarcane bagasse, corn based material, corn stover, wheat straw, rice straw, woody biomass, woody perennials, vascular plants and the like and their mixtures and their combinations. In one embodiment, the plant based raw material comprises wood based material or a mixture comprising wood based material. In one embodiment, the plant based raw material is wood based material or a mixture comprising wood based material. In one embodiment, the wood based material is selected from hardwood, softwood or their combination. In one embodiment, the plant based raw material comprises plant pieces, e.g. wood pieces.

In one embodiment, the plant based raw material (7) comprises carbohydrates and lignin.

Preferably, the carbohydrates have $C_n(H_2O)_n$ or $C_n(H_2O)_{n-1}$. The carbohydrates can comprise monosaccharides ($C_6H_{12}O_6$ or $C_5H_{10}O_5$) disaccharides ($C_{12}H_{22}O_{11}$), oligosaccharides and/or polysaccharides (($C_6H_{10}O_5)_n$ or ($C_5H_8O_4)_n$). Preferably, the plant based raw material comprises carbohydrates, such as soluble carbohydrates, e.g. C5 carbohydrates ($C_5H_{10}O_5$ or $C_5(H_2O)_n$), and solid carbohydrates, e.g. C6 carbohydrates ($C_6H_{12}O_6$ or $C_6(H_2O)_n$).

The plant based raw material (7) may contain one or more material components. Preferably, the plant based raw material is in the form of suspension which contains liquid, such as water. Preferably, the plant based raw material is treated to dissolve at least part of hemicellulose.

In one embodiment, the plant based raw material (7) has been pre-treated, preferably by means of a suitable pretreatment. The pre-treatment stage may be selected from the group consisting of physical pretreatment, such as milling, extrusion, microwave pretreatment, ultrasound pretreatment and freeze pretreatment, chemical pretreatment, such as acid pretreatment, alkaline pretreatment, ionic liquid pretreatment, organosolv pretreatment and ozonolysis, physicochemical pretreatment, such as steam explosion pretreatment, ammonia fiber explosion pretreatment, $CO_2$ explosion pretreatment, liquid hot water pretreatment and wet oxidation, biological pretreatment and their combinations. In one embodiment, the plant based raw material is treated by the hydrolysis, e.g. acid hydrolysis, autohydrolysis, thermal hydrolysis, supercritical hydrolysis and/or subcritical hydrolysis, in which at least a part of hemicellulose is separated from the raw material in connection with the hydrolysis. In one embodiment, the plant based raw material is treated by the steam explosion, in which hemicelluloses are treated and in which at least a part of polysaccharides of the hemicelluloses degrade into monosaccharides and oligosaccharides by means of a hydrolysis and in which pressure is rapidly released. In one embodiment, the plant based raw material is treated by the hydrolysis and by the steam explosion in one or more steps. In one embodiment, the plant based raw material is treated by the catalytic pretreatment, e.g. by using acid or base as catalyst. In the pretreatment stage the plant based raw material enters the reactor unit where the pretreatment takes place. The plant based raw material can be treated by means of one or more pretreatment. The treated plant based raw material (7) can be then supplied directly or via an intermediate step or via an intermediate storage to the enzymatic hydrolysis stage (2). Further, in one embodiment, the plant based raw material can be dewatered, e.g. by dewatering presses, and/or washed in one or two or more stages. The dewatering makes possible to separate sugar based streams.

In one embodiment, the plant based raw material (7) is diluted with liquid, preferably with water, e.g. fresh water or recirculated process water e.g. from a lignin purification process, or steam to form the feed to the enzymatic hydrolysis stage (2). Preferably, the plant based raw material is diluted to suitable solid content. Dilution water may be added before the enzymatic hydrolysis stage, such as in a mixing stage or before the mixing stage. In one embodiment, feed concentration of the plant based raw material is 2-60% by weight (TS, total solids, at 105° C.), preferably 4-40% by weight (TS, total solids at 105° C.), more preferable 10-30% by weight (TS, total solids, at 105° C.), into the enzymatic hydrolysis stage.

In one embodiment, the plant based raw material (7) is fed by means of any suitable feeding device, such as a pump, e.g. a mono pump or piston pump or other suitable pump, into the enzymatic hydrolysis stage (2). Selection of the feeding device is based on e.g. feed concentration and/or viscosity of the plant based raw material.

In one embodiment, the plant based raw material (7) or solid fraction (4,5,6,10,15,16,21,22,23) is fed to the enzymatic hydrolysis stage (2,8,17) as a uniform flow. In one embodiment, the plant based raw material (7) or solid fraction (4,5,6,10,15,16,21,22,23) is fed to the enzymatic hydrolysis stage (2,8,17) step by step or gradually for feeding material which have higher consistency than material in the enzymatic hydrolysis stage.

The method or apparatus may comprise one or more than one enzymatic hydrolysis stage (2,8,17). In one embodiment, the method or apparatus comprises one enzymatic hydrolysis stage. In one embodiment, the method or apparatus comprises more than one enzymatic hydrolysis stages. In one embodiment, the enzymatic hydrolysis stage is a continuous process stage. In one embodiment, the enzymatic hydrolysis stage is a batch process stage. In one embodiment, at least one enzymatic hydrolysis stage is a continuous stage, in a preferred embodiment at least the enzymatic hydrolysis stage to which a part (5,15,23) of the solid fraction is recirculated or from which a part (5,15,23) of solid fraction is recirculated is a continuous stage. In one embodiment, the method or apparatus comprises the first enzymatic hydrolysis stage (2) and the second enzymatic hydrolysis stage (8,17), e.g. a post enzymatic hydrolysis stage or lignin purification stage. In one embodiment, the first enzymatic hydrolysis stage is a continuous stage and the second enzymatic hydrolysis stage is a continuous stage or a batch stage. In one embodiment, the first enzymatic hydrolysis stage is a batch stage and the second enzymatic hydrolysis stage is a batch stage or continuous stage. In one embodiment, the method or apparatus comprises the first enzymatic hydrolysis stage (2), the second enzymatic hydrolysis stage (8), e.g. a post enzymatic hydrolysis stage, and the third enzymatic hydrolysis stage (17), e.g. a lignin purification stage. In one embodiment, the first enzymatic hydrolysis stage is a continuous stage, the second enzymatic hydrolysis stage is a continuous stage and the third enzymatic hydrolysis stage is a continuous stage or batch stage. In one embodiment, the first enzymatic hydrolysis stage is a continuous stage, the second enzymatic hydrolysis stage is a batch stage and the third enzymatic hydrolysis stage is a continuous stage or batch stage. In one embodiment, the first enzymatic hydrolysis stage is a batch stage, the second enzymatic hydrolysis stage is a batch stage and the third enzymatic hydrolysis stage is a batch stage or continuous stage. In one embodiment, the first enzymatic hydrolysis stage is a batch stage, the second enzymatic hydrolysis stage is a continuous stage and the third enzymatic hydrolysis stage is a continuous stage or batch stage. In one embodiment, the method or apparatus comprises more than three enzymatic hydrolysis stages.

In one embodiment, the enzymatic hydrolysis stage (2,8,17) comprises a reactor, vessel, container, other suitable device or their combination in which the enzymatic hydrolysis is carried out.

In one embodiment, at least one enzymatic hydrolysis stage (2,8,17) comprises at least one continuous enzymatic hydrolysis reactor. In one embodiment, at least one enzymatic hydrolysis stage (2,8,17) comprises at least one batch enzymatic hydrolysis reactor. In one embodiment, at least one enzymatic hydrolysis stage (2,8,17) comprises at least one continuous enzymatic hydrolysis reactor and at least one enzymatic hydrolysis stage (2,8,17) comprises at least one batch enzymatic hydrolysis reactor. In one embodiment, each continuous enzymatic hydrolysis stage (2,8,17) comprises at least one continuous enzymatic hydrolysis reactor.

In one embodiment, the plant based material, such as the plant based raw material (7) or the solid fraction (4,10,21), is hydrolysed in at least one enzymatic hydrolysis stage (2,8,17) with the enzymes. In one embodiment, the plant based raw material (7) is fed to the first enzymatic hydrolysis stage (2), and the solid fraction (4,10,21) separated after the enzymatic hydrolysis is fed to the next enzymatic hydrolysis stage (8,17) in which the solid fraction is treated.

The enzymatic hydrolysis stage (2,8,17) may comprise one or more enzymatic hydrolysis step or one or more enzymatic hydrolysis reactor. In one embodiment, the enzymatic hydrolysis stage comprises one enzymatic hydrolysis step or one enzymatic hydrolysis reactor. In one embodiment, the enzymatic hydrolysis stage comprises more than one enzymatic hydrolysis step or more than one enzymatic hydrolysis reactors.

In one embodiment, an average residence time in the first enzymatic hydrolysis stage (2) is below 72 hours, in one embodiment below 48 hours and in one embodiment below 24 hours. In one embodiment, the average residence time in the first enzymatic hydrolysis stage is over 4 hours, in one embodiment over 6 hours and in one embodiment over 8 hours. In one embodiment, the average residence time in the first enzymatic hydrolysis stage is between 4-72 hours, in one embodiment 6-48 hours and in one embodiment 8-24 hours.

In one embodiment, an average residence time in the second or any later enzymatic hydrolysis stage (8,17) is below 72 hours, in one embodiment below 48 hours and in one embodiment below 24 hours. In one embodiment, the average residence time in the second or any later enzymatic hydrolysis stage is over 4 hours, in one embodiment over 6 hours and in one embodiment over 8 hours. In one embodiment, the average residence time in the second or any later enzymatic hydrolysis stage is 4-72 hours, in one embodiment 6-48 hours and in one embodiment 8-24 hours. In one embodiment, the average residence time in the second enzymatic hydrolysis stage (8) is below 72 24 hours, in one embodiment below 48 hours and in one embodiment below 24 hours. In one embodiment, the average residence time in the second enzymatic hydrolysis stage is over 4 hours, in one embodiment over 6 hours and in one embodiment over 8 hours. In one embodiment, the average residence time in the second enzymatic hydrolysis stage is 4-72 hours, in one embodiment 6-48 hours and in one embodiment 8-24 hours. In one embodiment, the average residence time in the last enzymatic hydrolysis stage (17) depends on an amount of active enzyme in the last enzymatic hydrolysis stage. In one embodiment, the last enzymatic hydrolysis stage is performed without an enzyme addition. In one embodiment, an enzyme is added into the last enzymatic hydrolysis stage. In one embodiment, a purification of the solid fraction, e.g. lignin, is performed in the last enzymatic hydrolysis stage. In one embodiment, an amount of carbohydrates is below 30% by weight, preferably below 20% by weight, more preferably below 10% by weight, in the solid fraction (21) after the last enzymatic hydrolysis stage.

In one embodiment, the solid fraction (4,10,21) or its part (5,6,15,16,22,23) is diluted with liquid, preferably with water, e.g. fresh water or recirculated process water e.g. from a lignin purification process, or steam after the solid-liquid separation stage (11,12,18) and/or in connection with the enzymatic hydrolysis stage (2,8,17) and/or before supplying to the next enzymatic hydrolysis stage (8,17) and/or before the recirculation to the enzymatic hydrolysis stage (2,8,17). In one embodiment, the plant based feed (1) is diluted with liquid, preferably with water, e.g. fresh water or recirculated process water e.g. from a lignin purification process, or steam in connection with the enzymatic hydrolysis stage (2,8,17) and/or before the supplying to the enzymatic hydrolysis stage (2,8,17). Preferably, the solid fraction or the plant based feed is diluted to suitable solid content. In one embodiment, dilution water may be added before the enzymatic hydrolysis, such as in a mixing stage or before the mixing stage. In one embodiment, temperature of the enzymatic hydrolysis stage (2,8,17) is adjusted by means of temperature of the dilution liquid and/or by means of other suitable temperature control. In one embodiment, the solid fraction (4,10,21) or its part (5,6,15,16,22,23) or the plant based feed (1) is supplied without the dilution to the enzymatic hydrolysis stage (2,8,17).

In one embodiment, consistency of the plant based feed (1) or plant based raw material (7) is below 40%, in one embodiment below 30% and in one embodiment below 25% TS (total solids, at 105° C.) in the first enzymatic hydrolysis stage (2). In one embodiment, the consistency of the plant based feed or plant based raw material is over 4%, in one embodiment over 10% and in one embodiment over 15%, TS (at 105° C.) in the first enzymatic hydrolysis stage. In one embodiment, the consistency of the plant based feed or plant based raw material is 4-40% TS (at 105° C.), in one embodiment 10-30% TS (at 105° C.) and in one embodiment 15-25% TS (at 105 ° C.), in the first enzymatic hydrolysis stage. In one embodiment, the consistency of the plant based feed or plant based raw material is 4-10% TS (at 105° C.) in the first enzymatic hydrolysis stage.

In one embodiment, consistency of the plant based feed (1) or solid fraction (4,6,10,16,21,22) is below 40%, in one embodiment below 30%, in one embodiment below 25%, TS (total solids, at 105° C.) in the second or any later enzymatic hydrolysis stage (8,17). In one embodiment, the consistency of the plant based feed or solid fraction is over 10%, in one embodiment over 15%, in one embodiment over 16%, TS (at 105° C.) in the second or any later enzymatic hydrolysis stage. In one embodiment, the consistency of the plant based feed or solid fraction is 10-40%, in one embodiment 15-30%, in one embodiment 16-25%, TS (at 105° C.) in the second or any later enzymatic hydrolysis stage. In one embodiment, the consistency of the plant based feed or solid fraction is below 40%, in one embodiment below 30%, in one embodiment below 25%, TS (total solids, at 105° C.) in the second enzymatic hydrolysis stage (8). In one embodiment, the consistency of the plant based feed or solid fraction is over 10%, in one embodiment over 15%, in one embodiment over 16%, TS (at 105° C.) in the second enzymatic hydrolysis stage. In one embodiment, the consistency of the plant based feed or solid fraction is 10-40%, in one embodiment 15-30%, in one embodiment 16-25%, TS (at 105° C.) in the second enzymatic hydrolysis stage.

In one embodiment, the method comprises at least one mixing stage in connection with the enzymatic hydrolysis stage (2,8,17), e.g. before the enzymatic hydrolysis stage or in the enzymatic hydrolysis stage or during the enzymatic hydrolysis. In one embodiment, the method comprises the mixing stage in connection with the first enzymatic hydrolysis stage. In one embodiment, the method comprises the mixing stage in connection with the enzymatic hydrolysis stages following the first enzymatic hydrolysis stage, e.g. in connection with the second enzymatic hydrolysis stage or in connection with any enzymatic hydrolysis stage following the second enzymatic hydrolysis stage. In one embodiment, the method comprises the mixing stage in connection with any desired enzymatic hydrolysis stage. Preferably, the mixing is a mixing wherein there is sufficient shear force for mixing liquid and solids into a homogenous mixture during the mixing. Further, solids can be disintegrated by means of the effective mixing. Solid particles can break down leading to higher specific surface. In one embodiment, material temperature may be increased by 5-15° C. during the mixing stage. In one embodiment, the apparatus comprises at least one mixing device which may be selected from the group consisting of a mixer, screw mixer, pump, other suitable device or their combination.

In one embodiment, pH is adjusted before the enzymatic hydrolysis stage (2,8,17), e.g. in the mixing stage or before the mixing stage, or during the enzymatic hydrolysis stage. In one embodiment, pH is between 3-8, in one embodiment between 3.5-7 and in one embodiment between 4-6. In one embodiment, pH is adjusted so that pH is favorable for the enzyme used in the process.

In one embodiment, process conditions are adjusted in the enzymatic hydrolysis (2,8,17) so that the process conditions, such as temperature and pH and in one embodiment consistency, are favorable for the enzyme used in the process.

In one embodiment, dewatering is carried out after the enzymatic hydrolysis stage (2,8,17).

Preferably, the method and apparatus comprises at least one solid-liquid separation stage (11,12,18) preferably after the enzymatic hydrolysis stage (2,8,17). In one embodiment, the apparatus comprises at least one solid-liquid separation device. In one embodiment, the apparatus comprises more than one solid-liquid separation devices. In one embodiment, each solid-liquid separation stage (11,12,18) comprises at least one solid-liquid separation device. In one embodiment, the solid-liquid separation stage comprises more than one solid-liquid separation devices. In one embodiment, each solid-liquid separation stage comprises one solid-liquid separation device. In one embodiment, the liquid fraction (3,9,20) is separated from the solid fraction (4,10,21) by means of one solid-liquid separation device in more than one solid-liquid separation stages (11,12,18). In one embodiment, one solid-liquid separation device can be used in one or more solid-liquid separation stages (11,12, 18). In one embodiment, one solid-liquid separation device can be used in more than one solid-liquid separation stages. In one embodiment, the separation device comprises one or more separation step, e.g. separation segment.

The solid-liquid separation stage may comprise one or more separation steps. In one embodiment, the solid-liquid separation stage comprises different procedures which may be done in one or more separation steps. In one embodiment, the liquid fraction is separated in one step. Alternatively, the liquid fraction may be separated in more than one step. In one embodiment, the liquid fraction is separated in each separation step.

In one embodiment, at least one solid-liquid separation stage (11,12,18) is arranged in connection with the enzymatic hydrolysis stage (2,8,17). In one embodiment, one solid-liquid separation stage (11,12,18) is arranged after the enzymatic hydrolysis stage (2,8,17). In one embodiment, one solid-liquid separation stage (11,12,18) is arranged after the last enzymatic hydrolysis step or reactor (2c) of the enzymatic hydrolysis stage (2,8,17). In one embodiment, the solid-liquid separation stage is arranged after desired enzymatic hydrolysis steps or reactors (2a,2b,2c) of the enzymatic hydrolysis stage (2,8,17). In one embodiment, the solid-liquid separation stage is arranged after each enzymatic hydrolysis steps or reactors (2a,2b,2c) of the enzymatic hydrolysis stage (2,8,17).

Preferably, the solid-liquid separation stage (11,12,18) comprises the separation of the liquid fraction (3,9,20) from the solids, such as the solid fraction (4,10,21). In one embodiment, the liquid fraction is separated from the solid fraction by means of filtration, centrifugal treatment or their combinations. In one embodiment, the filtration is carried out by pressure, underpressure or overpressure.

In one embodiment, the solid-liquid separation device is based on a countercurrent washing. In one embodiment, the solid-liquid separation device is selected from the group consisting of filtration device, vacuum filtration device, press filter, belt press, centrifugal device, screw press and their combinations. In one embodiment, the solid-liquid separation device is selected from the group consisting of pressure filtration device, vacuum filtration device, filtration device based on underpressure, filtration device based on overpressure, filter press, other suitable press, centrifugal device and their combinations. In one embodiment, the solid-liquid separation device is a pressure filtration device, vacuum filtration device, filtration device based on underpressure or filtration device based on overpressure. In one embodiment, the solid-liquid separation device is a belt press, twin wire press or centrifuge. Alternatively, the solid-liquid separation device can be another washing device in which low amount of washing water is used and washing is done in high dry matter content. Then good recovery can be achieved. Alternatively, the solid-liquid separation device may be any suitable separation device.

In one embodiment, the solid-liquid separation stage (11,12,18) comprises a filtration in which the liquid fraction (3,9,20) is separated in a liquid form and solid material is formed. Preferably, pressure is used in the filtration. In one embodiment, liquid is separated by a pressure difference, such as by means of vacuum or overpressure. In one embodiment, the solid-liquid separation stage comprises a washing in which a displacement washing is carried out with small amount clean water in order to remove majority of sugars, inhibitors and other soluble compounds from the solid fraction (4,10,21) and to provide high recovery of soluble compounds. Preferably, ratio of washing water to solid is below 6, preferably below 3 and more preferably below 1.5. In one embodiment, the solid-liquid separation stage (11,12,18) comprises the filtration and washing. Preferably, high concentration and recovery of soluble material in the liquid phase can be achieved with small amount of clean water. Further, the solid fraction with minor amount of soluble compounds, or the solid fraction which is substantially free of soluble compounds, or the soluble compound lean solid fraction, can be achieved.

In one embodiment, the liquid fraction (3,9,20) is separated by means of a pressure filtration. In one embodiment, the apparatus comprises at least one pressure filtration device as the solid-liquid separation device.

In the different solid-liquid separation stages the separation can be carried out by means of similar or different separation methods or separation devices.

In one embodiment, the apparatus comprises at least one means for supplying the intermediate product (30,31,32) from the enzymatic hydrolysis stage (2,8,17) to the solid-liquid separation stage (11,12,18). In one embodiment, the means for supplying the intermediate product (30,31,32) is selected from the group consisting of conveyor, screw, belt, pump, pipe, tube, duct, conduit, channel, outlet, other suitable feeding device and their combinations.

In one embodiment, the apparatus comprises at least one means for supplying the solid fraction (4,6,10,16,21,22) to the next enzymatic hydrolysis stage (8,17). In one embodiment, the means for supplying the solid fraction is selected from the group consisting of conveyor, screw, belt, pump, pipe, tube, duct, conduit, channel, outlet, other suitable feeding device and their combinations.

In one embodiment, the apparatus comprises at least one means or at least one device for separating a part (5,15,23) of the solid fraction in order to recirculate to the enzymatic hydrolysis, e.g. to any enzymatic hydrolysis stage (2,8,17). Further, the apparatus comprises preferably at least one recirculation device for recirculating at least a part (5,15,23) of at least one solid fraction (4,10,21) comprising enzymes to the plant based feed (1) of the enzymatic hydrolysis stage (2,8,17) or to the enzymatic hydrolysis stage (2,8,17), in one embodiment to the plant based feed (1) of any enzymatic hydrolysis stage (2,8,17), such as the same or previous enzymatic hydrolysis stage or a next enzymatic hydrolysis stage, or to any enzymatic hydrolysis stage (2,8,17), such as back to the same or previous enzymatic hydrolysis stage or to a next enzymatic hydrolysis stage.

In one embodiment, the part (5,15,23) of the solid fraction (4,10,21) may be recirculated in connection with at least one enzymatic hydrolysis stage (2,8,17). In one embodiment, the part of the solid fraction is recirculated in connection with one enzymatic hydrolysis stage. In one embodiment, the part of the solid fraction is recirculated in connection with more than one enzymatic hydrolysis stages. In one embodiment, the part (5) of the solid fraction is recirculated in connection with the first enzymatic hydrolysis stage (2). In one embodiment, the part (15) of the solid fraction is recirculated in connection with the second enzymatic hydrolysis stage (8). In one embodiment, the part (23) of the solid fraction is recirculated in connection with the third enzymatic hydrolysis stage (17). In one embodiment, the part of the solid fraction is recirculated in connection with each enzymatic hydrolysis stage. In one embodiment, the part of the solid fraction is recirculated to the desired previous enzymatic hydrolysis stage. In one embodiment, the part of the solid fraction is recirculated back to the same enzymatic hydrolysis stage. In one embodiment, the part of solid fraction is recirculated to the next enzymatic hydrolysis stage. In one embodiment, the part of the solid fraction from at least one predetermined enzymatic hydrolysis stage is recirculated in connection with the desired enzymatic hydrolysis stage. In a preferred embodiment, the part of the solid fraction is recirculated to such enzymatic hydrolysis stage in which a glucose-lignin ratio is bigger than in the recirculated solid fraction (5,15,23).

In one embodiment, the method or apparatus comprises one recirculation device and the enzymatic hydrolysis stage (2,8,17) comprising one enzymatic hydrolysis reactor. In one embodiment, the method or apparatus comprises one recirculation device and the enzymatic hydrolysis stage (2,8,17) comprising more than one enzymatic hydrolysis reactors (2a,2b,2c). In one embodiment, the method or apparatus comprises more than one recirculation devices and the enzymatic hydrolysis stage (2,8,17) comprising more than one enzymatic hydrolysis reactors (2a,2b,2c). In one embodiment, the part of solid fraction is recirculated to the desired step (2a,2b,2c) of the enzymatic hydrolysis stage (2,8,17).

In one embodiment, the method comprises more than one the enzymatic hydrolysis stages (2,8,17), and at least a part (5,15,23) of at least one solid fraction (4,10,21) comprising enzymes is recirculated to the plant based feed (1) of at least one enzymatic hydrolysis stage (2,8,17) or to at least one enzymatic hydrolysis stage (2,8,17). In one embodiment, the apparatus comprises more than one the enzymatic hydrolysis stages (2,8,17), and at least one recirculation device is arranged to recirculate at least a part (5,15,23) of at least one solid fraction (4,10,21) comprising enzymes to the plant based feed (1) of at least one enzymatic hydrolysis stage (2,8,17) or to at least one enzymatic hydrolysis stage (2,8,17).

In one embodiment, the method comprises more than one the enzymatic hydrolysis stages (2,8,17), and at least a part (5,15,23) of at least one solid fraction (4,10,21) comprising enzymes is recirculated back to the plant based feed (1) of the same enzymatic hydrolysis stage (2,8,17) or to the same enzymatic hydrolysis stage (2,8,17), and a rest part (6,16,22) of the solid fraction (4,10,21) is supplied to the next enzymatic hydrolysis stage (8,17). In one embodiment, the apparatus comprises more than one enzymatic hydrolysis stages (2,8,17), and the recirculation device for recirculating at least a part (5,15,23) of at least one solid fraction (4,10,21) comprising enzymes back to the plant based feed (1) of the same enzymatic hydrolysis stage (2,8,17) or to the same enzymatic hydrolysis stage (2,8,17), and means for supplying a rest part (6,16,22) of the solid fraction (4,10,21) to the next enzymatic hydrolysis stage (8,17).

In one embodiment, a part (5,15,23) of the solid fraction (4,10,21) comprising enzymes is recirculated back to the plant based feed (1) of the same or previous enzymatic hydrolysis stage (2,8,17).

In one embodiment, a part (5,15,23) of the solid fraction (4,10,21) comprising enzymes is recirculated back to the same or previous enzymatic hydrolysis stage (2,8,17). In one embodiment, a part (5,15,23) of the solid fraction (4,10,21) comprising enzymes is recirculated to the plant based feed (1) of any enzymatic hydrolysis stage (2,8,17), e.g. next or later enzymatic hydrolysis stage, or to any enzymatic hydrolysis stage (2,8,17), e.g. next or later enzymatic hydrolysis stage. Preferably, the most of the enzymes are attached on the solid fraction. In one embodiment, the feed of the enzymatic hydrolysis stage (2,8,17) comprises plant based feed (1) of 10-90% by weight, in one embodiment 20-60% by weight and in one embodiment 25-35% by weight. In one embodiment, the feed of the enzymatic hydrolysis stage (2,8,17) comprises recirculated solid fraction (5,15,23) of 10-90% by weight, in one embodiment 40-80% by weight and in one embodiment 65-75% by weight.

In one embodiment, when the state of equilibrium of the process is achieved, the mass (% by weight) of the lignin in the recovered solid fraction (6,16,22) is substantially equal than the mass (% by weight) of the lignin in the fresh plant based feed (1) which is fed to the enzymatic hydrolysis stage.

In one embodiment, the enzyme (13,14,24) is added in connection with the enzymatic hydrolysis stage (2,8,17). In one embodiment, the enzyme is added in the mixing stage or before the mixing stage. In one embodiment, the apparatus comprises an addition device for adding the enzyme. In one embodiment, the enzyme (13,14,24) is added in connection with the enzymatic hydrolysis stage (2,8,17) to which at least a part (5,15,23) of the solid fraction (4,10,21) comprising enzymes is recirculated. In one embodiment, the enzyme (13) is added in connection with the first enzymatic hydrolysis stage (2). In one embodiment, the enzyme (13,14,24) is added to the plant based feed (1). In one embodiment, the enzyme (13,14,24) is added to the enzymatic hydrolysis stage (2,8,17). In one embodiment, the enzyme is added to the solid fraction (4,6,10,16,21,22) before the enzymatic hydrolysis stage (2,8,17) or during the enzymatic hydrolysis. In one embodiment, the enzyme (13,14,24) is added to the recirculated solid fraction (5,15,23). In one embodiment, the enzyme (13,14,24) is added in any enzymatic hydrolysis stage (2,8,17) such as in the first (2), second (8) or any later enzymatic hydrolysis stage (17), e.g. in a lignin purification stage. In one embodiment, the enzyme is added in connection with the enzymatic hydrolysis stage (2,8,17), such as before the enzymatic hydrolysis stage or during the enzymatic hydrolysis. Preferably, the enzyme (13,14,24) is added to the stage or step in which the process conditions are favorable for the enzyme used in the process or in which the enzyme is not denatured. In one embodiment, the enzyme dose is 30-70%, in one embodiment 40-60%, in one embodiment 45-55%, by weight from the reference enzyme dose in the reference enzymatic hydrolysis stage. In one embodiment, the enzyme dose is optimized based on the material of the feed, properties of the enzyme and/or desired conversion. In one embodiment, the enzymatic hydrolysis stage (2,8,17) in which at least a part (5,15) of the solid fraction (4,10,21) comprising enzymes is recirculated back to the plant based feed (1) is carried out without an enzyme addition.

In one embodiment, the enzyme is not added in the second or any later enzymatic hydrolysis stage (8,17). In one embodiment, the second or any later enzymatic hydrolysis stage (8,17) is carried out without an enzyme addition. It has been surprisingly observed that the second or any later enzymatic hydrolysis can be initiated and the enzymatic hydrolysis proceeds without the enzyme addition. Further, it has been observed that the enzyme is going on the solid fraction and the enzyme of the previous enzymatic hydrolysis stage (2,8) can be supplied to the next enzymatic hydrolysis stage (8,17) together with the solid fraction. In one embodiment, the enzyme is selected so that the enzyme has adhesion ability to the solids. In one embodiment, the recycled enzyme is activated during the mixing.

In one embodiment, the apparatus comprises at least one means for recovering the solid fraction (4,10,21) or its part (6,16,22) after the solid-liquid separation stage (11,12,18), e.g. any solid-liquid separation stage. In one embodiment, the means for recovering the solid fraction is selected from the group consisting of assembly, outlet, conveyor, screw, belt, pipe, tube, duct, discharge outlet, discharge valve, discharge channel, conduit, other suitable device and their combinations.

In one embodiment, at least one liquid fraction (3,9,20) is recovered after the solid-liquid separation stage (11,12,18), e.g. any solid-liquid separation stage. In one embodiment, the apparatus comprises at least one means for recovering at least one liquid fraction after the solid-liquid separation stage (11,12,18). In one embodiment, the means for recovering the liquid fraction is selected from the group consisting of assembly, outlet, pipe, tube, duct, discharge outlet, discharge valve, discharge channel, conduit, other suitable device and their combinations. In one embodiment, at least two liquid fractions (3,9,20) are combined. In one embodiment, all the liquid fractions are combined.

In one embodiment, the liquid fraction (3,9,20) is formed by means of the method. In one embodiment, the liquid fraction comprises soluble C5 and C6 carbohydrates after the enzymatic hydrolysis stage (2,8,17), e.g. after the first enzymatic hydrolysis stage (2). In one embodiment, the liquid fraction comprises soluble C6 carbohydrates after the enzymatic hydrolysis stage. In one embodiment, the liquid fraction (9,20) comprises soluble C6 carbohydrates, and further it may comprise also C5 carbohydrates, preferably below 20%, more preferably below 10%, the most preferably below 5%, by weight of the carbohydrates, after the second or any later enzymatic hydrolysis stage (8,17). Preferably, the liquid fraction (3,9,20) can contain other monosaccharides, disaccharides, oligosaccharides and/or polysaccharides. In one embodiment, the liquid fraction (3,9,20) contains galactose, glucose, mannose, arabinose, xylose, glucuronic acid and galacturonic acid. Preferably, the liquid fraction is in the form of solution.

In one embodiment, at least a part of the liquid fraction (3,9,20) is recovered by supplying out from the solid-liquid separation stage (11,12,18). In one embodiment, at least 50%, preferably at least 60%, more preferably at least 70%, of the soluble carbohydrates is supplied out from the first solid-liquid separation stage (11).

In one embodiment, at least 50%, preferably at least 60%, more preferably at least 70%, of the soluble carbohydrates is supplied out from the second or any later solid-liquid separation stage (12,18). In one embodiment, the liquid fraction (12,18) comprises C6 carbohydrates over 80% by weight, preferably over 90% by weight, the most preferably over 95% by weight, of the carbohydrates. Preferably, the liquid fraction (12,18) is a glucose rich fraction. Then the liquid fraction (12,18) is sufficient pure that it can be used as such, or it can be concentrated and utilized after the concentration.

The liquid fraction (3,9,20) may be used as component in manufacturing a final product. The liquid fractions from the different solid-liquid separation stages (11,12,18) can be utilized separately, or they can be combined or mixed and utilized as a mixture. In one embodiment, the liquid fraction is used as such. In one embodiment, the liquid fraction is supplied to a further processing. In one embodiment, the liquid fraction is purified. In one embodiment, the liquid fraction is concentrated. In one embodiment, the monomerization of the liquid fraction is made before the further processing. In one embodiment, the liquid fraction is supplied to a fermentation process. In one embodiment, the liquid fraction is used as a source material in the fermentation. In one embodiment, the liquid fraction is supplied to a hydrolysis process. In one embodiment, the liquid fraction is used as a source material in the hydrolysis, such as in the acid hydrolysis, enzymatic hydrolysis or the like. In one embodiment, the liquid fraction is supplied to a chemical treatment process. In one embodiment, the liquid fraction is used as a source material in the chemical treatment. In one embodiment, the liquid fraction is supplied to a polymerization process. In one embodiment, the liquid fraction is used as a source material in the polymerization process. In one embodiment, the liquid fraction is supplied to a depolymerization process. In one embodiment, the liquid fraction is used as a source material in the depolymerization process. In one embodiment, the liquid fraction is supplied to a catalytic treatment process. In one embodiment, the liquid fraction is used as a source material in the catalytic treatment. In one embodiment, the liquid fraction is supplied to a degradation process. In one embodiment, the liquid fraction is used as a source material in the degradation process. In one embodiment, the liquid fraction is supplied to an enzymatic treatment. In one embodiment, the liquid fraction is used as a source material in the enzymatic treatment. In one embodiment, the liquid fraction is supplied to a manufacture of binder. In one embodiment, the liquid fraction is used as a source material in the manufacture of binder. In one embodiment, the liquid fraction is supplied to a manufacture of feed. In one embodiment, the liquid fraction is used as a source material in the manufacture of feed. In one embodiment, the liquid fraction is supplied to a manufacture of food. In one embodiment, the liquid fraction is used as a source material in the manufacture of food. The liquid fraction may be supplied directly to the fermentation, hydrolysis, chemical treatment, catalytic treatment, polymerization process, depolymerization process, degradation process, enzymatic treatment, manufacture of binder, manufacture of feed, manufacture of food or other suitable process or their combinations, or alternatively via a suitable treatment step or an additional step, e.g. additional concentration step or purification step, to the fermentation, hydrolysis, chemical treatment, catalytic treatment, polymerization process, depolymerization process, degradation process, enzymatic treatment, manufacture of binder, manufacture of feed, manufacture of food or other suitable process or their combinations.

Preferably, the solid fraction (4,10,21) comprising solids is formed by means of the method. In one embodiment, the solid fraction (4,10,21) comprises lignin after the solid-liquid separation stage (11,12,18). In one embodiment, the solid fraction comprises lignin and solid carbohydrates, such as C6carbohydrates, such as $(C_6H_{12}O_6$ or $(C_6(H_2O)_n)$, and other solid carbohydrates after the solid-liquid separation stage. Further, the solid fraction may comprise some residual soluble material. Preferably, the solid fraction comprises also enzymes. Preferably, the most of the enzymes are attached on the solid fraction. In one embodiment, the solid fraction is in the form of a solid material. In one embodiment, dry matter content of the solid material is over 30% by weight, preferably over 40% by weight, more preferably over 50% by weight, after the solid-liquid separation stage. In one embodiment, dry matter content of the solid material is 15-80% by weight, in one embodiment 20-70% by weight, in one embodiment 30-60% by weight and in one embodiment 40-60% by weight, after the solid-liquid separation stage. In one embodiment, the solid fraction contains soluble compounds below 15%, preferably below 6%, more preferably below 3% by weight, after the solid-liquid separation stage. In one embodiment, an amount of carbohydrates is below 25% by weight, preferably below 10% by weight, more preferably below 5% by weight, in the solid fraction.

In one embodiment, at least a part (6,16,22) of the solid fraction (4,10,21) is recovered after the solid-liquid separation stage (11,12,18). In one embodiment, a part (6,16,22) of the solid fraction (4,10,21) is supplied out after the solid-liquid separation stage (11,12,18). In one embodiment, a part (6,16,22) of the solid fraction (4,10,21) is supplied to the next enzymatic hydrolysis stage (8,17).

The solid fraction (4,6,10,16,21,22) may be used as component in manufacturing a final product. In one embodiment, the solid fraction is used as such. In one embodiment, the solid fraction is supplied to a further processing. In one embodiment, the solid fraction (4,6,10,16) is supplied to a lignin purification (17) for forming purified lignin. In one embodiment, the solid fraction (4,6,10,16,21,22) is supplied to a lignin separation for separating lignin from the solid fraction. In one embodiment, the solid fraction (4,6,10,16,21,22) is supplied to a hydrolysis which may be selected from the group consisting of acid hydrolysis, enzymatic hydrolysis, supercritical hydrolysis and/or subcritical hydrolysis and their combinations, or to a polymerization process, a depolymerization process, a degradation process, a chemical treatment, a manufacture of a composite material, lignin composite, activated carbon, carbon fiber, binder material, polymers, resins, phenolic component, dispersion agent or absorbent material, a manufacture of feed or food, or a combustion process or other suitable process or their combinations. The solid fraction (4,6,10,16,21,22) may be supplied directly to the hydrolysis, polymerization process, depolymerization process, degradation process, chemical treatment, manufacturing processes of said materials, combustion process or other suitable process, or alternatively via a suitable treatment step or an additional step, e.g. additional separation step, purification step or dewatering step, to the hydrolysis, polymerization process, depolymerization process, degradation process, chemical treatment, manufacturing processes of said materials, combustion process or other suitable process.

In one embodiment, lignin is separated in a lignin separation stage from the solid fraction (21,22) after the last solid-liquid separation stage (18). Preferably, lignin is purified in connection with the enzymatic hydrolysis stage (17), e.g. the last enzymatic hydrolysis stage, and/or the lignin separation stage. In one embodiment, the apparatus comprises at least one lignin separation device or lignin purification device. The lignin can be utilized as such, e.g. as a component in the final product or in the combustion. Alternatively, the lignin can be supplied to a further processing.

By means of the method and the apparatus the enzymatic hydrolysis can be improved and the enzyme dosage can be decreased. The enzymes can be recycled in the method or in the apparatus. Then the costs of the enzymes may be decreased in the process. Further, by means of the method and the apparatus the process may be run continuously. Further, by means of the method and the apparatus residence time or reaction time of the enzymatic hydrolysis can be shortened, consistency can be increased in the enzymatic hydrolysis, purity of lignin can be improved, and/or the conversion of carbohydrates can be improved. In the method and apparatus an effective enzymatic hydrolysis can be achieved.

The method and the apparatus can be used for treating materials comprising inhibitors, and for manufacturing lignin, carbohydrates and chemicals, and for removing inhibitors. In one process inhibitors, preferably inhibitors coming from cellulose based material, may be removed. According to an example, the inhibitor may belong to the group consisting of soluble lignin, organic acids, dissolved salts, glucose, xylose, oligomers, or other inhibitors or their combinations. Simultaneously, the recovery of the liquid fraction and solid fraction can be improved, and more pure solid fraction comprising lignin, can be formed.

The method and the apparatus provide the solid fraction and liquid fraction with good quality. The solid fraction has very high concentration of lignin. Further, the solid fraction has very high purity. When inhibitors are removed together with the liquid fraction, more purified solid fraction can be provided in the process. Further, raw material with inhibitors and undesired agents can be used as a source material in the process. Also the carbohydrate recovery and conversion can be improved. Further, the method and the apparatus decrease post-treating costs of the solid fraction and also liquid fraction.

The method and the apparatus provide an industrially applicable, simple and affordable way of carrying out the enzymatic hydrolysis. The method or the apparatus is easy and simple to realize as a production process. The method and the apparatus are suitable for use in the manufacture of the different lignin and sugar based fractions and final products from different starting materials.

EXAMPLES

Some embodiments of the invention are described in more detail by the following examples with reference to accompanying drawings.

Example 1

In this example, the enzymatic hydrolysis comprising a predetermined enzyme dose is carried out in one stage in which a solid fraction with enzymes is recirculated, and a solid fraction and liquid fraction are produced according to a process of FIG. 1.

Plant based raw material (7) is fed by means of a feeding device as a plant based feed (1) into a continuous enzymatic hydrolysis stage (2) which comprises a continuous plug flow enzymatic hydrolysis reactor. The plant based raw material has been treated by means of pre-treatment, e.g. by physical, chemical or physic-chemical treatment such as by microwave or ultrasound treatment, or by steam explosion. The plant based feed (1) may be diluted with liquid before the enzymatic hydrolysis stage (2). After the enzymatic hydrolysis stage (2), the apparatus comprises a solid-liquid separation stage (11) comprising a filtration device or a centrifugal device. A liquid fraction (3) comprising soluble C5 and C6 carbohydrates is separated from a solid fraction (4) in the solid-liquid separation stage (11). The liquid fraction (3) is recovered. The solid fraction (4) containing e.g. lignin, solid carbohydrates, some soluble sugar, oligomer and polymer residual is removed from the solid-liquid separation stage (11).

A main part (5) of the solid fraction (4) comprising enzymes is recirculated by means of a recirculation device back to the plant based feed (1) of the enzymatic hydrolysis stage (2) or to the enzymatic hydrolysis stage (2). Preferably, fresh enzyme (13) is added to the plant based feed (1), or alternatively to the enzymatic hydrolysis stage (2) or to the recirculated solid fraction (5). Alternatively, fresh enzyme (13) is not added. The solid fraction (5) may be diluted with liquid before the enzymatic hydrolysis stage (2).

A rest part (6) of the solid fraction (4) comprising enzymes is recovered, and it may be supplied to the next treatment stage. The apparatus may comprise means for supplying the solid fraction (6) out from the apparatus or means for supplying the solid fraction (6) to the next treatment stage.

Example 2

In this example, the enzymatic hydrolysis comprising a predetermined enzyme dose is carried out in two stages in which a solid fraction with enzymes is recirculated in at least one stage, and a solid fraction and liquid fraction are produced according to a process of FIG. 2.

Plant based raw material (7) is fed by means of a feeding device as a plant based feed (1) into a first continuous enzymatic hydrolysis stage (2) which comprises a continuous plug flow enzymatic hydrolysis reactor. The plant based raw material has been treated by means of pre-treatment, e.g. by physical, chemical or physic-chemical treatment such as by microwave or ultrasound treatment, or by steam explosion. The plant based feed (1) may be diluted with liquid before the first enzymatic hydrolysis stage (2).

After the first enzymatic hydrolysis stage (2), the apparatus comprises a first solid-liquid separation stage (11) comprising a filtration device or a centrifugal device. An intermediate product (30) of the first enzymatic hydrolysis is supplied into the solid-liquid separation stage (11). A liquid fraction (3) comprising soluble C5 and C6 carbohydrates is separated from a solid fraction (4) in the solid-liquid separation stage (11). The liquid fraction (3) is recovered. The solid fraction (4) containing e.g. lignin, solid carbohydrates, some soluble sugar, oligomer and polymer residual is removed from the solid-liquid separation stage (11).

A main part (5) of the solid fraction (4) comprising enzymes is recirculated by means of a recirculation device back to the plant based feed (1) of the enzymatic hydrolysis stage (2) or to the enzymatic hydrolysis stage (2). Preferably, fresh enzyme (13) is added to the plant based feed (1), or alternatively to the enzymatic hydrolysis stage (2) or to the recirculated solid fraction (5). The solid fraction (5) may be diluted with liquid before the enzymatic hydrolysis stage (2).

A rest part (6) of the solid fraction (4) comprising enzymes is recovered, and it is supplied to the second continuous, or alternatively batch, enzymatic hydrolysis stage (8), e.g. to the post enzymatic hydrolysis stage. The apparatus may comprise means for supplying the solid fraction (6) to the second enzymatic hydrolysis stage (8). The solid fraction (6) may be diluted with liquid before the second enzymatic hydrolysis. Enzyme (14) may be added to the solid fraction (6) or to the second enzymatic hydrolysis stage (8). Alternatively, the second enzymatic hydrolysis stage (8) may be performed without the enzyme addition.

After the second enzymatic hydrolysis stage (8), an intermediate product (31) of the enzymatic hydrolysis is supplied into a second solid-liquid separation stage (12) comprising a filtration device or a centrifugal device. A liquid fraction (9) comprising soluble C6 carbohydrates is separated from a solid fraction (10) in the solid-liquid separation stage (12). The liquid fraction (9) is recovered. In one embodiment, the second liquid fraction (9) is combined to the first liquid fraction (3). A solid fraction (10) containing e.g. lignin, some solid carbohydrates and some soluble carbohydrates is removed from the separation stage (12) and is recovered after the solid-liquid separation stage.

Example 3

In this example, the enzymatic hydrolysis comprising a predetermined enzyme dose is carried out in three stages in which a solid fraction with enzymes is recirculated in at least one stage, and a solid fraction and liquid fraction are produced according to a process of FIG. 3.

Plant based raw material (7) with enzymes (13) is fed by means of a feeding device into a first continuous enzymatic hydrolysis stage (2) which comprises a continuous plug flow enzymatic hydrolysis reactor. The plant based raw material has been treated by means of pre-treatment, e.g. by physical, chemical or physic-chemical treatment such as by microwave or ultrasound treatment, or by steam explosion. The plant based raw material (7) may be diluted with liquid before the first enzymatic hydrolysis stage (2).

After the first enzymatic hydrolysis stage (2), the apparatus comprises a first solid-liquid separation stage (11) comprising a filtration device or a centrifugal device. An intermediate product (30) of the first enzymatic hydrolysis is supplied into the solid-liquid separation stage (11). A liquid fraction (3) comprising soluble C5 and C6 carbohydrates is separated from a solid fraction (4) in the solid-liquid separation stage (11). The liquid fraction (3) is recovered. The solid fraction (4) containing e.g. lignin, solid carbohydrates, some soluble sugar, oligomer and polymer residual is removed from the solid-liquid separation stage (11).

The solid fraction (4) comprising enzymes is supplied as a plant based feed (1) to the second continuous enzymatic hydrolysis stage (8). The apparatus may comprise means for supplying the solid fraction (4) to the second enzymatic hydrolysis stage (8). The solid fraction (4) may be diluted with liquid before the second enzymatic hydrolysis.

After the second enzymatic hydrolysis stage (8), an intermediate product (31) of the enzymatic hydrolysis is supplied into a second solid-liquid separation stage (12) comprising a filtration device or a centrifugal device. A liquid fraction (9) comprising soluble C6 carbohydrates is separated from a solid fraction (10) in the solid-liquid separation stage (12). The liquid fraction (9) is recovered. In one embodiment, the second liquid fraction (9) is combined to the first liquid fraction (3). A solid fraction (10) containing e.g. lignin, some solid carbohydrates and some soluble carbohydrates is removed from the separation stage (12).

A main part (15) of the solid fraction (10) comprising enzymes is recirculated by means of a recirculation device back to the plant based feed (1) of the second enzymatic hydrolysis stage (8) or to the second enzymatic hydrolysis stage (8). Preferably, fresh enzyme (14) is added to the plant based feed (1), or alternatively to the second enzymatic hydrolysis stage (8) or to the recirculated solid fraction (15). The solid fraction (15) may be diluted with liquid before the enzymatic hydrolysis stage (8).

A rest part (16) of the solid fraction (10) comprising enzymes is recovered, and it is supplied to the third enzymatic hydrolysis stage (17), e.g. to the lignin purification stage. The apparatus may comprise means for supplying the solid fraction (16) to the third enzymatic hydrolysis stage (17). The solid fraction (16) may be diluted with liquid before the third enzymatic hydrolysis. The third enzymatic hydrolysis stage (17) may be performed without the enzyme addition. Alternatively, enzyme may be added to the solid fraction (16) or to the third enzymatic hydrolysis stage (17).

After the third enzymatic hydrolysis stage (17), an intermediate product (32) of the enzymatic hydrolysis is supplied into a third solid-liquid separation stage (18) comprising a filtration device or a centrifugal device. A liquid fraction (20) comprising soluble C6 carbohydrates is separated from a solid fraction (21) in the solid-liquid separation stage (18). The liquid fraction (20) is recovered. In one embodiment, the third liquid fraction (20) is combined to the first liquid fraction (3). A solid fraction (21) containing e.g. lignin, some solid carbohydrates and some soluble carbohydrates is removed from the separation stage (18) and is recovered after the solid-liquid separation stage.

In one embodiment, lignin may be separated from the solid fraction (21) in a lignin separation stage comprising a lignin separation device. The enzymes are denatured in the lignin separation stage.

Example 4

In this example, the enzymatic hydrolysis comprising a predetermined enzyme dose is carried out in two stages in which a solid fraction with enzymes is recirculated in at least one stage, and a solid fraction and liquid fraction are produced according to a process of FIG. 4.

Plant based raw material (7) is fed by means of a feeding device as a plant based feed (1) into a first continuous enzymatic hydrolysis stage (2) which comprises three enzymatic hydrolysis steps (2a,2b,2c) with continuous plug flow enzymatic hydrolysis reactors. The plant based raw material has been treated by means of pre-treatment, e.g. by physical, chemical or physic-chemical treatment such as by microwave or ultrasound treatment, or by steam explosion. The plant based feed (1) may be diluted with liquid before the first enzymatic hydrolysis step (2a) of the first enzymatic hydrolysis stage (2).

After the first enzymatic hydrolysis stage (2), the apparatus comprises a first solid-liquid separation stage (11) comprising a filtration device or a centrifugal device. An intermediate product (30) of the last enzymatic hydrolysis step (2c) of the first enzymatic hydrolysis (2) is supplied into the solid-liquid separation stage (11). A liquid fraction (3)

comprising soluble C5 and C6 carbohydrates is separated from a solid fraction (4) in the solid-liquid separation stage (11). The liquid fraction (3) is recovered. The solid fraction (4) containing e.g. lignin, solid carbohydrates, some soluble sugar, oligomer and polymer residual is removed from the solid-liquid separation stage (11).

A main part (5) of the solid fraction (4) comprising enzymes is recirculated by means of a recirculation device back to the plant based feed (1) of the enzymatic hydrolysis stage (2) or between the predetermined enzymatic hydrolysis steps (2a,2b,2c) of the enzymatic hydrolysis stage (2). Preferably, fresh enzyme (13) is added to the plant based feed (1), or alternatively to the predetermined enzymatic hydrolysis step (2a,2b,2c) of the enzymatic hydrolysis stage (2) or to the recirculated solid fraction (5). The solid fraction (5) may be diluted with liquid before the enzymatic hydrolysis stage (2) or before the predetermined enzymatic hydrolysis step (2a,2b,2c).

A rest part (6) of the solid fraction (4) comprising enzymes is recovered, and it is supplied to the second continuous, or alternatively batch, enzymatic hydrolysis stage (8), e.g. to the post enzymatic hydrolysis stage. The apparatus may comprise means for supplying the solid fraction (6) to the second enzymatic hydrolysis stage (8). The solid fraction (6) may be diluted with liquid before the second enzymatic hydrolysis. Enzyme (14) may be added to the solid fraction (6) or to the second enzymatic hydrolysis stage (8). Alternatively, the second enzymatic hydrolysis stage (8) may be performed without the enzyme addition.

After the second enzymatic hydrolysis stage (8), an intermediate product (31) of the enzymatic hydrolysis is supplied into a second solid-liquid separation stage (12) comprising a filtration device or a centrifugal device. A liquid fraction (9) comprising soluble C6 carbohydrates is separated from a solid fraction (10) in the solid-liquid separation stage (12). The liquid fraction (9) is recovered. In one embodiment, the second liquid fraction (9) is combined to the first liquid fraction (3). A solid fraction (10) containing e.g. lignin, some solid carbohydrates and some soluble carbohydrates is removed from the separation stage (12) and is recovered after the solid-liquid separation stage.

Example 5

In this example, the enzymatic hydrolysis comprising a predetermined enzyme dose is carried out in three stages in which a solid fraction with enzymes is recirculated in all three stages, and a solid fraction and liquid fraction are produced according to a process of FIG. 5.

Plant based raw material (7) is fed by means of a feeding device as a first plant based feed (7,1) into a first continuous enzymatic hydrolysis stage (2) which comprises a continuous plug flow enzymatic hydrolysis reactor. The plant based raw material may be treated according to Example 1.

After the first enzymatic hydrolysis stage (2), the apparatus comprises a first solid-liquid separation stage (11) comprising a filtration device or a centrifugal device. An intermediate product (30) of the first enzymatic hydrolysis is supplied into the solid-liquid separation stage (11). A liquid fraction (3) comprising soluble C5 and C6 carbohydrates is separated from a solid fraction (4) in the solid-liquid separation stage (11). The liquid fraction (3) is recovered. The solid fraction (4) containing e.g. lignin, solid carbohydrates, some soluble sugar, oligomer and polymer residual is removed from the solid-liquid separation stage (11). A main part (5) of the solid fraction (4) comprising enzymes is recirculated by means of a recirculation device back to the plant based feed (7,1) of the enzymatic hydrolysis stage (2) or to the first enzymatic hydrolysis stage (2). Fresh enzyme (13) may be added to the plant based feed (7,1), or alternatively to the first enzymatic hydrolysis stage (2) or to the recirculated solid fraction (5). The solid fraction (5) may be diluted with liquid before the enzymatic hydrolysis stage (2).

A rest part (6) of the solid fraction (4) comprising enzymes is supplied as a second plant based feed (6,1) to the second continuous enzymatic hydrolysis stage (8). The apparatus may comprise means for supplying the solid fraction (6) to the second enzymatic hydrolysis stage (8). The solid fraction (6) may be diluted with liquid before the second enzymatic hydrolysis.

After the second enzymatic hydrolysis stage (8), an intermediate product (31) of the enzymatic hydrolysis is supplied into a second solid-liquid separation stage (12) comprising a filtration device or a centrifugal device. A liquid fraction (9) comprising soluble C6 carbohydrates is separated from a solid fraction (10) in the solid-liquid separation stage (12). The liquid fraction (9) is recovered. In one embodiment, the second liquid fraction (9) is combined to the first liquid fraction (3). A solid fraction (10) containing e.g. lignin, some solid carbohydrates and some soluble carbohydrates is removed from the separation stage (12). A main part (15) of the solid fraction (10) comprising enzymes is recirculated by means of a recirculation device back to the plant based feed (6,1) of the second enzymatic hydrolysis stage (8) or to the second enzymatic hydrolysis stage (8). Fresh enzyme (14) may be added to the plant based feed (6,1), or alternatively to the second enzymatic hydrolysis stage (8) or to the recirculated solid fraction (15). The solid fraction (15) may be diluted with liquid before the enzymatic hydrolysis stage (8).

A rest part (16) of the solid fraction (10) comprising enzymes is recovered, and it is supplied to the third enzymatic hydrolysis stage (17), e.g. to the lignin purification stage. The apparatus may comprise means for supplying the solid fraction (16) as a plant based feed (16,1) to the third enzymatic hydrolysis stage (17). The solid fraction (16) may be diluted with liquid before the third enzymatic hydrolysis. The third enzymatic hydrolysis stage (17) may be performed without the enzyme addition. Alternatively, enzyme (24) may be added to the solid fraction (16) or to the third enzymatic hydrolysis stage (17).

After the third enzymatic hydrolysis stage (17), an intermediate product (32) of the enzymatic hydrolysis is supplied into a third solid-liquid separation stage (18) comprising a filtration device or a centrifugal device. A liquid fraction (20) comprising soluble C6 carbohydrates is separated from a solid fraction (21) in the solid-liquid separation stage (18). The liquid fraction (20) is recovered. In one embodiment, the third liquid fraction (20) is combined to the first liquid fraction (3). A solid fraction (21) containing e.g. lignin, some solid carbohydrates and some soluble carbohydrates is removed from the separation stage (18). A main part (23) of the solid fraction (21) comprising enzymes is recirculated by means of a recirculation device back to the plant based feed (16,1) of the enzymatic hydrolysis stage (17) or to the third enzymatic hydrolysis stage (17). Fresh enzyme (24) may be added to the plant based feed (16,1), or alternatively to the third enzymatic hydrolysis stage (17) or to the recirculated solid fraction (23). A rest part (22) of the solid fraction (21) is recovered after the solid-liquid separation stage (18). In one embodiment, lignin may be separated from the solid fraction (22) in a lignin separation stage comprising a lignin separation device. The enzymes are denatured in the lignin separation stage.

Example 6

In this example, an enzymatic hydrolysis and a recirculation in connection with an enzymatic hydrolysis process were studied.

One step enzymatic hydrolysis process with enzyme recycling was simulated and compared to a traditional batch hydrolysis process in laboratory scale tests. Dilute acid pretreated and steam exploded birch was used as a substrate in the test. Composition of the substrate was: glucane 44.7% by weight, xylane 20.8% by weight and lignin 24.2% by weight.

Commercially available enzyme mixture A was used in the hydrolysis. The substrate was diluted by using distilled water and pH was adjusted to 5, temperature was 50° C., enzyme dosages were 2% and 4% (based on dry matter content of substrate, total solids TS, at 105° C.) for references and 2% (based on dry matter content of substrate, total solids TS, at 105° C.) with recycling. Initial dry matter content (total solids TS, at 105° C.) was 15% in the experiments. 3 liter reactor with mixing and 1.5 liter slurry volume was used for the hydrolysis. In case of the enzyme recycling the reactor slurry was taken from the reactor always after 24 hour hydrolysis time and dewatered with Buchner funnel into 30% dry matter content (total solids TS, at 105° C.). Recycling ratio of recycled solid material:new substrate in reactor feed was 2:1. Sugar content was analyzed from the liquid fraction using standard HPLC methods, standard SCAN CM 71:09. The reference samples were taken after 12, 49 and 73 hours from traditional batch type of process.

Figure 6:
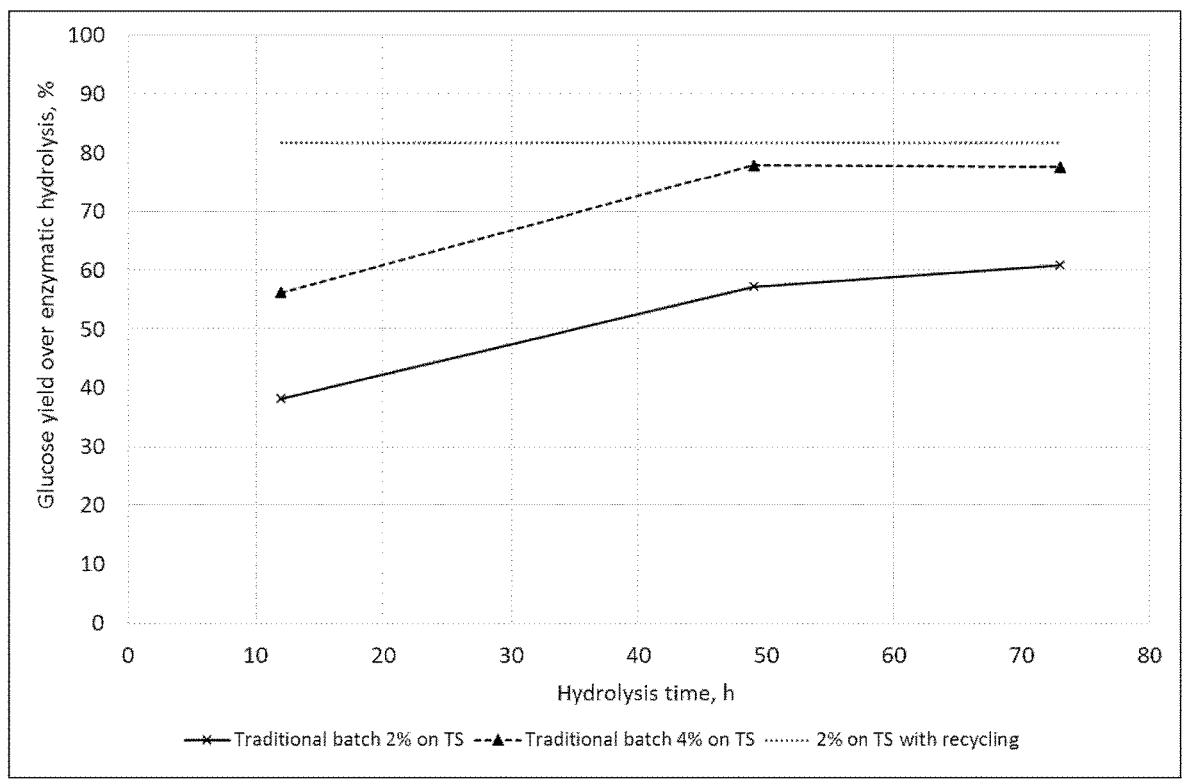
FIG. 6 shows results from one example carried out according to one method embodiment.

From FIG. 6 it can be seen that final glucose yield of the reference with 2% dosage was 60.8% and with 4% dosage 77.7%. 2% enzyme dosage with the recycling gave 81.7% final yield at the state of equilibrium of the process.

Example 7

In this example, an enzymatic hydrolysis and a recirculation in connection with an enzymatic hydrolysis were studied.

Two step enzymatic hydrolysis process with enzyme recycling was tested and compared to a traditional one step batch hydrolysis process in laboratory scale tests. Dilute acid pretreated and steam exploded birch was used as a substrate in the test. Composition of the substrate was: glucane 44.7%, xylane 20.8% and lignin 24.2% by weight.

Commercially available enzyme mixture A was used in the hydrolysis. The substrate was diluted by using distilled water and pH was adjusted to 5, temperature was 50° C., enzyme dosage was 1.3% (based on dry matter content of substrate, total solids TS, at 105° C.) and initial dry matter content of the slurry (total solids TS, at 105° C.) was 14% in the experiments. 3 liter reactor with 1.5 liter slurry volume and mixing was used for the first hydrolysis step, and 50 ml tubes containing 20 g of slurry was put into a mixer and the mixer was placed in an incubator for the post hydrolysis step.

The reactor slurry was taken from the reactor always after 10 hour hydrolysis time (1st hydrolysis step with the recycling) and dewatered with Buchner funnel into 30% dry matter content (total solids TS, at 105° C.). Sugar content was analyzed from the liquid fraction using standard HPLC methods, standard SCAN CM 71:09. Recycling ratio of recycled solid material:new substrate was 2:1.

Residual solids was diluted back to 14% dry matter content (total solids TS, at 105° C.) for the post hydrolysis step and put into 50 ml tubes, 20 ml slurry/tube. Tubes were put into a mixer and the mixer was placed in an incubator. Samples of the second hydrolysis step were taken out from the incubator after 24 and 48 hours. The tubes were put in a centrifuge, rotating speed 1000 rpm with 5 minutes running time. A solid liquid separation was done by taking the liquid phase out from the tube. Sugar analysis was done using standard HPLC methods, standard SCAN CM 71:09.

Figure 7:
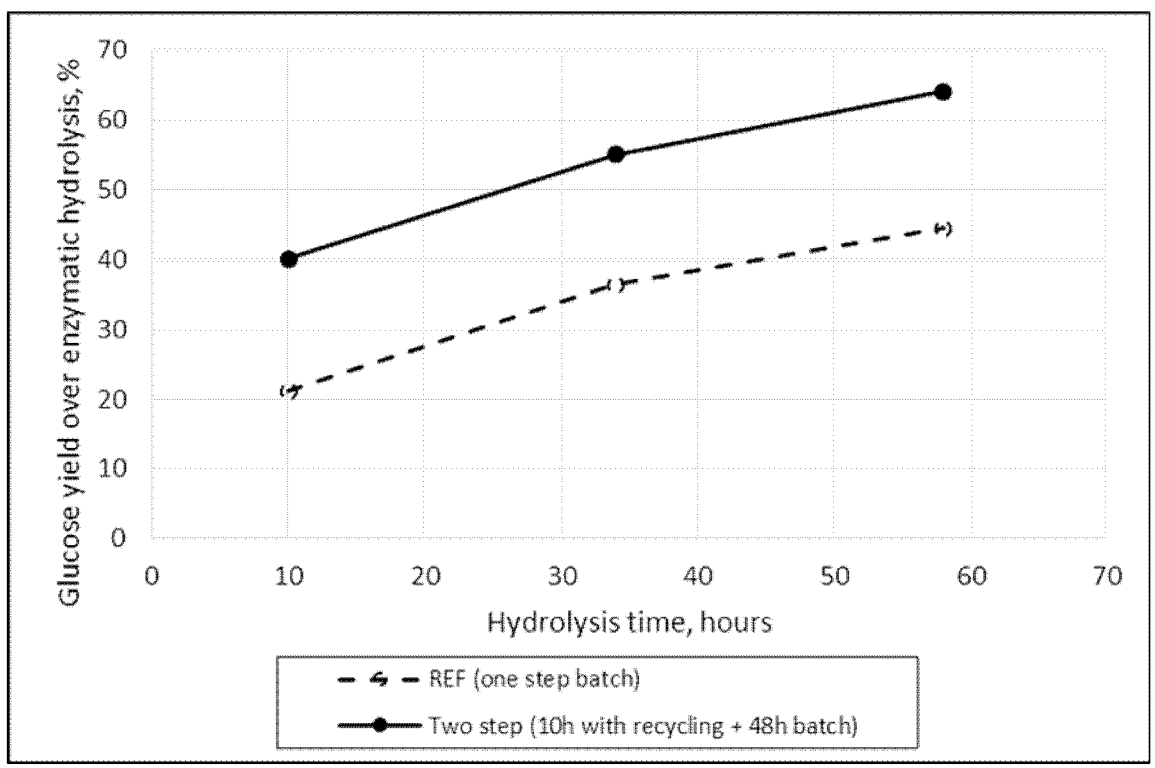
FIG. 7 shows results from one example carried out according to one method embodiment.

From FIG. 7 it can be seen that final glucose yield of the reference was 44.5% and for the two step process with the recycling was 64.1% at the state of equilibrium of the process. Then almost 20% units higher yield was achieved.

Example 8

In this example, an enzymatic hydrolysis and a recirculation in connection with an enzymatic hydrolysis were studied.

Two step enzymatic hydrolysis process with enzyme recycling was simulated and compared to a traditional one step batch hydrolysis process in laboratory scale tests. Autohydrolysis pretreated and steam exploded birch was used as a substrate in the test. Composition of the substrate was: glucane 52.7%, xylane 7.9% and lignin 26.4% by weight.

Commercially available enzyme mixture B was used in the hydrolysis. The substrate was diluted by using distilled water and pH was adjusted to 4.5, temperature was 45° C., enzyme dosage was 7% (based on dry matter content of substrate, total solids TS, at 105° C.) for the reference and 3% (based on dry matter content of substrate, total solids TS, at 105° C.) with the recycling. Initial dry matter content (total solids TS, at 105° C.) was 6% for the reference because of poor mixing properties and 10% with the recycling in the first step and 18% in the second step because of improved mixing properties of the material by partial hydrolysis of dry matter. 3 liter reactor with 1.5 liter slurry volume and mixing was used for the first hydrolysis step and 50 ml tubes containing 20 g of slurry was put into a mixer and the mixer was placed in an incubator for the post hydrolysis step.

The reactor slurry was taken from the reactor always after 8 hour hydrolysis time (1st hydrolysis step with the recycling) and dewatered with Buchner funnel into 34% dry matter content (total solids TS, at 105° C.). Sugar content was analyzed from the liquid fraction using standard HPLC methods standard SCAN CM 71:09. Recycling ratio of recycled solid material:new substrate was 5:3.

Residual solids was diluted back to 18% dry matter content (total solids TS, at 105° C.) for the post hydrolysis step and put into 50 ml tubes, 20 ml slurry/tube. The tubes were put into a mixer and the mixer was placed in an incubator. Samples of the second hydrolysis step were taken out from the incubator after 48 hours. The tubes were put in a centrifuge, rotating speed 1000 rpm with 5 minutes running time. A solid liquid separation was done by taking the liquid phase out from the tube. Sugar analysis was done using standard HPLC methods standard SCAN CM 71:09.

Final glucose yield of the reference was 77.2% with 7% enzyme dosing on TS after 72 hour hydrolysis time, and 77.7% with 3% enzyme dosing on TS combined with the recycling in the first hydrolysis step and 48 hours post hydrolysis step at the state of equilibrium of the process. In addition to savings in enzyme costs also clearly smaller reactors were needed for the hydrolysis due to higher consistencies in case of the recycling and two-step process.

Example 9

In this example, an enzymatic hydrolysis and a recirculation in connection with an enzymatic hydrolysis were studied.

One step enzymatic hydrolysis process with enzyme recycling was simulated and compared to a traditional batch hydrolysis process in laboratory scale tests. Organosolv pretreated and steam exploded hardwood mixture was used as a substrate in the test. Composition of the substrate was: glucane 70.5%, xylane 6.8% and lignin 8.9% by weight.

Commercially available enzyme mixture A was used in the hydrolysis. The substrate was diluted by using distilled water and pH was adjusted to 5, temperature was 50° C., enzyme dosages was 2% (based on dry matter content of substrate, total solids TS, at 105° C.) for references and 1% (based on dry matter content of substrate, total solids TS, at 105° C.) with the recycling. Initial dry matter content was 10% (total solids TS, at 105° C.) in the experiments. Dry matter content for the references was 10% (total solids TS, at 105° C.) and residence time was 60 hours. 3 liter reactor with mixing and 1.5 liter slurry volume was used for the hydrolysis. In case of the enzyme recycling the reactor slurry was taken from the reactor always after 30 hour hydrolysis time and dewatered with Buchner funnel into 28% dry matter content (total solids TS, at 105° C.). Recycling ratio of recycled solid material:new substrate in reactor feed was 1:1. Sugar content was analyzed from the liquid fraction using standard HPLC methods, standard SCAN CM 71:09. Reference samples were taken after 60 hours from the traditional batch type process.

Final glucose yield of the reference with 2% dosage was 77.1%. 1% enzyme dosage with the recycling gave 80.4% final yield at the state of equilibrium of the process.

Example 10

In this example, an enzymatic hydrolysis and a recirculation in connection with an enzymatic hydrolysis were studied.

Two step enzymatic hydrolysis process with enzyme recycling was simulated and compared to a traditional one step batch hydrolysis process in laboratory scale tests. Autohydrolysis pretreated, steam exploded and alkaline treated birch was used as a substrate in the test. Composition of the substrate was: glucane 71.2%, xylane 4.0% and lignin 14.7% by weight.

Commercially available enzyme mixture C was used in the hydrolysis. The substrate was diluted by using distilled water and pH was adjusted to 5, temperature was 50° C., enzyme dosages were 8% and 10% (based on dry matter content of substrate, total solids TS, at 105° C.) for references and 3% (based on dry matter content of substrate, total solids TS, at 105° C.) with the recycling. Initial dry matter content was 15% (total solids, at 105° C.) in the experiments. 3 liter reactor with 1.5 liter slurry volume and mixing was used for the first hydrolysis step and 50 ml tubes containing 20 g of slurry was put into a mixer and the mixer was placed in an incubator for the post hydrolysis step.

The reactor slurry was taken from the reactor always after 14 hour hydrolysis time (1st hydrolysis step with the recycling) and dewatered with Büchner funnel into 27% dry matter content (total solids TS, at 105° C.). Sugar content was analyzed from the liquid fraction using standard HPLC methods, standard SCAN CM 71:09. Recycling ratio of recycled solid material:new substrate was 4:3.

Residual solids was diluted back to 15% dry matter content (total solids TS, at 105° C.) for the post hydrolysis step and put into 50 ml tubes, 20 ml slurry/tube. The tubes were put into a mixer and the mixer was placed in an incubator. Samples of the second hydrolysis step were taken out from the incubator after 24 and 48 hours. The tubes were put in a centrifuge, rotating speed 1000 rpm with 5 minutes running time. A solid liquid separation was done by taking the liquid phase out from the tube. Sugar analysis was done using standard HPLC methods, standard SCAN CM 71:09.

Figure 8:
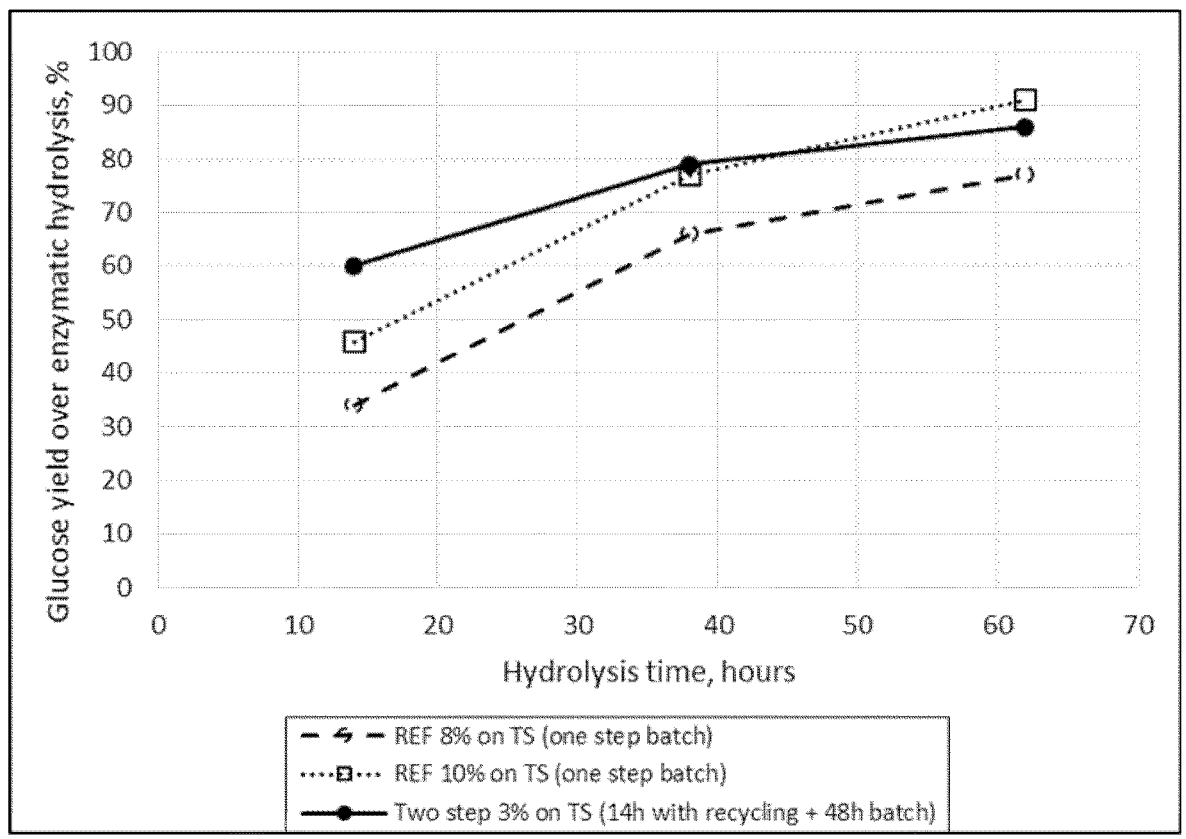
FIG. 8 shows results from one example carried out according to one method embodiment.

From FIG. 8 it can be seen that final glucose yield of the reference with 8% dosage was 77% and with 10% dosage 91%. 3% enzyme dosage with the recycling gave 86% final yield for glucose at the state of equilibrium of the process.

The method and apparatus according to the present invention is suitable in different embodiments to be used in different enzymatic hydrolysis. Further, the method and apparatus according to the present invention is suitable in different embodiments to be used for producing the most different kinds of liquid and solid fractions from different raw materials.

The invention is not limited merely to the example referred to above; instead many variations are possible within the scope of the inventive idea defined by the claims.

The invention claimed is:

1. A method for an enzymatic hydrolysis in which wood based material is hydrolysed using enzymes in at least one enzymatic hydrolysis stage, the method comprising:
   pretreating the wood based material using a combination of hydrolysis and steam explosion to form a wood based feed wherein the wood based feed comprises cellulose based material;
   feeding the wood based feed to the enzymatic hydrolysis stage in which the wood based feed is hydrolysed;
   separating a liquid fraction comprising carbohydrates from a solid fraction in a solid-liquid separation stage wherein most of the enzymes are attached to the solid fraction;
   recirculating at least a part of the solid fraction comprising the enzymes to the wood based feed of the same or previous enzymatic hydrolysis stage; and
   recovering a rest part of the solid fraction.

2. The method according to claim 1, wherein the at least one enzymatic hydrolysis stage is more than one enzymatic hydrolysis stage, and the at least a part of the solid. fraction comprising enzymes is recirculated to the wood based feed of at least one of the enzymatic hydrolysis stages or to at least one of the enzymatic hydrolysis stages.

3. The method according to claim 1, wherein the at least one enzymatic hydrolysis stage is more than one enzymatic hydrolysis stage, and the at least a part of the solid fraction comprising enzymes is recirculated back to the wood based feed of the same enzymatic hydrolysis stage or to the same enzymatic hydrolysis stage, and the rest part of the solid fraction is supplied to a next enzymatic hydrolysis stage.

4. The method according to claim 1, wherein an average residence time of the at least one enzymatic hydrolysis stage is 4-72 hours.

5. The method according to claim I, wherein a consistency of the wood based feed is 4-40% by weight in the at least one enzymatic hydrolysis stage.

6. The method according to claim 1, wherein the at least one enzymatic hydrolysis stage is more than one enzymatic hydrolysis stage, and a consistency of the wood based feed or the solid fraction is 10-40% by weight in a second or any later enzymatic hydrolysis stage.

7. The method according to claim 1. further comprising: diluting the rest part of the solid fraction with liquid; and supplying the diluted rest part of the solid fraction to a next enzymatic hydrolysis stage or other treatment stage.

8. The method according claim 1, wherein the liquid fraction is separated from the solid fraction using filtration, centrifugal treatment, or a combination thereof.

9. The method according to claim 1, wherein the liquid fraction is recovered after the solid-liquid separation stage.

10. The method according to claim 1, wherein a feed of the at least one enzymatic hydrolysis stage comprises the wood based feed of 20-60% by weight and the recirculated solid fraction of 40-80% by weight.

11. The method according to claim 1, wherein the at least one enzymatic hydrolysis stage is more than one enzymatic hydrolysis stage, the method further comprising adding an enzyme in connection with a first enzymatic hydrolysis stage or a second or later enzymatic hydrolysis stage or the enzymatic hydrolysis stage to which the at least a part of the solid fraction is recirculated.

12. The method according to claim 1, wherein the at least one enzymatic hydrolysis stage is more than one enzymatic hydrolysis stage, and a second or any later enzymatic hydrolysis stage is carried out without an enzyme addition.

13. The method according to claim 1, wherein the wood based feed is thrilled from a wood based raw material, the wood based raw material being a wood based material or a mixture comprising a wood based material.

14. The method according to claim 1, wherein the fraction is configured to be used as a source material in a fermentation, hydrolysis, chemical treatment, catalytic treatment, polymerization process, depolymerization process, degradation process, enzymatic treatment, manufacture of binder, manufacture of feed, manufacture of food, or any combination thereof.

15. The method according to claim 1, wherein the solid fraction is configured to be used as a source material in a hydrolysis, polymerization process, depolymerization process, degradation process, chemical treatment, manufacture of a composite material, lignin composite, activated carbon, carbon fiber, binder material, polymers, resins, phenolic component, dispersion agent or absorbent material, manufacture of feed, manufacture of food, combustion process or other suitable process or their combinations.

\* \* \* \* \*